United States Patent
Wardle et al.

(10) Patent No.: US 10,406,025 B2
(45) Date of Patent: Sep. 10, 2019

(54) OCULAR IMPLANTS AND METHODS FOR DELIVERING OCULAR IMPLANTS INTO THE EYE

(71) Applicant: IVANTIS, INC., Irvine, CA (US)

(72) Inventors: John Wardle, San Clemente, CA (US); Andrew T. Schieber, Irvine, CA (US); Kenneth M. Galt, Laguna Hills, CA (US)

(73) Assignee: IVANTIS, INC., Irvine, CA (US)

( * ) Notice: Subject to any disclaimer, the term of this patent is extended or adjusted under 35 U.S.C. 154(b) by 785 days.

(21) Appl. No.: 14/932,658

(22) Filed: Nov. 4, 2015

(65) Prior Publication Data

US 2016/0051406 A1 Feb. 25, 2016

Related U.S. Application Data

(63) Continuation of application No. 13/865,770, filed on Apr. 18, 2013, now Pat. No. 9,211,213, which is a
(Continued)

(51) Int. Cl.
*A61F 9/00* (2006.01)
*A61F 9/007* (2006.01)

(52) U.S. Cl.
CPC .......... *A61F 9/0017* (2013.01); *A61F 9/0026* (2013.01); *A61F 9/00781* (2013.01)

(58) Field of Classification Search
CPC .......... A61M 127/002; A61F 9/00781
(Continued)

(56) References Cited

U.S. PATENT DOCUMENTS

| 703,296 A | 6/1902 | Arnold |
| 1,601,709 A | 10/1926 | Windom |

(Continued)

FOREIGN PATENT DOCUMENTS

| AU | 1998/76197 B2 | 2/1999 |
| CN | 1950091 A | 4/2007 |

(Continued)

OTHER PUBLICATIONS

Bahler, et al.; Trabecular bypass stents decrease intraocular pressure in cultured human anterior segments; Amer. Journal of Ophthalmology; vol. 138, No. 6; pp. 988-994.e2; Dec. 2004.

(Continued)

*Primary Examiner* — Leslie R Deak
(74) *Attorney, Agent, or Firm* — Shay Glenn LLP

(57) ABSTRACT

An ocular implant is provided. In some embodiments, the ocular implant includes a body that is curved about a longitudinal central axis and a distal body portion that defines a longitudinal channel including a channel opening. The implant is sized and configured such that the ocular implant assumes an orientation in which the channel opening is adjacent a major side of Schlemm's canal when the ocular implant is disposed in Schlemm's canal. Methods for delivering ocular implants into Schlemm's canal are also provided. Some methods include covering openings in the ocular implant, advancing the implant into Schlemm's canal while at least some of the openings are covered, and uncovering the openings while the distal portion of the implant is disposed in Schlemm's canal.

14 Claims, 29 Drawing Sheets

Related U.S. Application Data continuation of application No. 12/833,863, filed on Jul. 9, 2010, now Pat. No. 8,425,449.

(60) Provisional application No. 61/224,158, filed on Jul. 9, 2009.

(58) Field of Classification Search
USPC .................................. 604/8, 9; 606/107, 108
See application file for complete search history.

(56) References Cited

U.S. PATENT DOCUMENTS

| | | |
|---|---|---|
| 2,716,983 A | 9/1955 | George et al. |
| 3,071,135 A | 1/1963 | Baldwin et al. |
| 3,788,327 A | 1/1974 | Donowitz et al. |
| 3,811,442 A | 5/1974 | Maroth |
| 3,858,577 A | 1/1975 | Bass et al. |
| 3,884,236 A | 5/1975 | Krasnov |
| 3,948,271 A | 4/1976 | Akiyama |
| 3,982,541 A | 9/1976 | L'Esperance |
| 4,037,604 A | 7/1977 | Newkirk |
| 4,134,405 A | 1/1979 | Smit |
| 4,273,109 A | 6/1981 | Enderby |
| 4,391,275 A | 7/1983 | Fankhauser et al. |
| 4,428,746 A | 1/1984 | Mendez |
| 4,457,757 A | 7/1984 | Molteno |
| 4,461,294 A | 7/1984 | Baron |
| 4,470,407 A | 9/1984 | Hussein |
| 4,497,319 A | 2/1985 | Sekine et al. |
| 4,501,274 A | 2/1985 | Skjaerpe |
| 4,517,973 A | 5/1985 | Sunago et al. |
| 4,538,608 A | 9/1985 | L'Esperance |
| 4,551,129 A | 11/1985 | Coleman et al. |
| 4,558,698 A | 12/1985 | O'Dell |
| 4,559,942 A | 12/1985 | Eisenberg |
| 4,566,438 A | 1/1986 | Liese et al. |
| 4,580,559 A | 4/1986 | L'Esperance |
| 4,583,539 A | 4/1986 | Karlin et al. |
| 4,601,713 A | 7/1986 | Fuquo |
| 4,604,087 A | 8/1986 | Joseph |
| 4,633,866 A | 1/1987 | Peyman et al. |
| 4,658,816 A | 4/1987 | Ector |
| 4,660,546 A | 4/1987 | Herrick et al. |
| 4,671,273 A | 6/1987 | Lindsey |
| 4,689,040 A | 8/1987 | Thompson |
| 4,699,140 A | 10/1987 | Holmes et al. |
| 4,706,669 A | 11/1987 | Schlegel |
| 4,722,350 A | 2/1988 | Armeniades et al. |
| 4,722,724 A | 2/1988 | Schocket |
| 4,729,373 A | 3/1988 | Peyman |
| 4,733,665 A | 3/1988 | Palmaz |
| 4,750,901 A | 6/1988 | Molteno |
| 4,770,654 A | 9/1988 | Rogers et al. |
| 4,791,927 A | 12/1988 | Menger |
| 4,826,478 A | 5/1989 | Schocket |
| 4,846,172 A | 7/1989 | Berlin |
| 4,861,341 A | 8/1989 | Woodburn |
| 4,876,250 A | 10/1989 | Clark |
| 4,880,000 A | 11/1989 | Holmes et al. |
| 4,886,488 A | 12/1989 | White |
| 4,919,130 A | 4/1990 | Stoy et al. |
| 4,925,299 A | 5/1990 | Meisberger et al. |
| 4,934,363 A | 6/1990 | Smith et al. |
| 4,934,809 A | 6/1990 | Volk |
| 4,936,825 A | 6/1990 | Ungerleider |
| 4,946,436 A | 8/1990 | Smith |
| 4,968,296 A | 11/1990 | Ritch et al. |
| 4,994,060 A | 2/1991 | Rink et al. |
| 5,034,010 A | 7/1991 | Kittrell et al. |
| 5,092,837 A | 3/1992 | Ritch et al. |
| 5,123,902 A | 6/1992 | Muller et al. |
| 5,127,901 A | 7/1992 | Odrich |
| 5,129,895 A | 7/1992 | Vassiliadis et al. |
| 5,178,604 A | 1/1993 | Baerveldt et al. |
| 5,180,362 A | 1/1993 | Worst |
| 5,190,552 A | 3/1993 | Kelman |
| 5,213,569 A | 5/1993 | Davis |
| 5,246,452 A | 9/1993 | Sinnott |
| 5,254,112 A | 10/1993 | Sinofsky et al. |
| 5,273,056 A | 12/1993 | McLaughlin et al. |
| 5,290,267 A | 3/1994 | Zimmermann |
| 5,300,020 A | 4/1994 | L'Esperance |
| 5,359,685 A | 10/1994 | Waynant et al. |
| 5,360,399 A | 11/1994 | Stegmann |
| 5,371,078 A | 12/1994 | Clark et al. |
| 5,372,577 A | 12/1994 | Ungerleider |
| 5,445,637 A | 8/1995 | Bretton |
| 5,454,796 A | 10/1995 | Krupin |
| 5,458,615 A | 10/1995 | Klemm et al. |
| 5,501,274 A | 3/1996 | Nguyen et al. |
| 5,536,259 A | 7/1996 | Utterberg |
| 5,575,780 A | 11/1996 | Saito |
| 5,591,223 A | 1/1997 | Lock et al. |
| 5,607,966 A | 3/1997 | Hellberg et al. |
| 5,613,972 A | 3/1997 | Lee et al. |
| 5,626,558 A | 5/1997 | Suson |
| 5,643,250 A | 7/1997 | O'Donnell |
| 5,653,753 A | 8/1997 | Brady et al. |
| 5,657,760 A | 8/1997 | Ying et al. |
| 5,676,669 A | 10/1997 | Colvard |
| 5,704,907 A | 1/1998 | Nordquist et al. |
| 5,713,844 A | 2/1998 | Peyman |
| 5,722,970 A | 3/1998 | Colvard et al. |
| 5,736,491 A | 4/1998 | Patel et al. |
| 5,738,676 A | 4/1998 | Hammer et al. |
| 5,738,677 A | 4/1998 | Colvard et al. |
| 5,785,658 A | 7/1998 | Benaron et al. |
| 5,792,099 A | 8/1998 | DeCamp et al. |
| 5,792,103 A | 8/1998 | Schwartz et al. |
| 5,807,302 A | 9/1998 | Wandel |
| 5,811,453 A | 9/1998 | Yanni et al. |
| 5,865,831 A | 2/1999 | Cozean et al. |
| 5,868,697 A | 2/1999 | Richter et al. |
| 5,879,319 A | 3/1999 | Pynson et al. |
| 5,885,279 A | 3/1999 | Bretton |
| 5,893,837 A | 4/1999 | Eagles et al. |
| 5,895,831 A | 4/1999 | Brasier et al. |
| 5,919,171 A | 7/1999 | Kira et al. |
| 5,948,427 A | 9/1999 | Yamamoto et al. |
| 5,968,058 A | 10/1999 | Richter et al. |
| 5,990,099 A | 11/1999 | Clark |
| 5,993,438 A | 11/1999 | Juhasz et al. |
| 5,997,531 A | 12/1999 | Loeb et al. |
| 6,002,480 A | 12/1999 | Izatt et al. |
| 6,007,511 A | 12/1999 | Prywes |
| 6,050,970 A | 4/2000 | Baerveldt |
| 6,083,193 A | 7/2000 | Kadziauskas et al. |
| 6,099,521 A | 8/2000 | Shadduck |
| 6,102,045 A | 8/2000 | Nordquist et al. |
| 6,146,375 A | 11/2000 | Juhasz et al. |
| 6,177,544 B1 | 1/2001 | Kanai et al. |
| 6,186,974 B1 | 2/2001 | Allan et al. |
| 6,217,584 B1 | 4/2001 | Nun |
| 6,221,078 B1 | 4/2001 | Bylsma |
| 6,238,409 B1 | 5/2001 | Hojeibane |
| 6,241,721 B1 | 6/2001 | Cozean et al. |
| D444,874 S | 7/2001 | Haffner et al. |
| 6,297,228 B1 | 10/2001 | Clark |
| 6,319,274 B1 | 11/2001 | Shadduck |
| 6,328,747 B1 | 12/2001 | Nun |
| 6,375,642 B1 | 4/2002 | Grieshaber et al. |
| 6,398,809 B1 | 6/2002 | Hoffmann et al. |
| 6,409,752 B1 | 6/2002 | Boatman et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,517,523 B1 | 2/2003 | Kaneko et al. |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |

(56) References Cited

U.S. PATENT DOCUMENTS

| | | |
|---|---|---|
| 6,551,289 B1 | 4/2003 | Higuchi et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,702,790 B1 | 3/2004 | Ross |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,899,717 B2 | 5/2005 | Weber et al. |
| 6,939,298 B2 | 9/2005 | Brown et al. |
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B2 | 1/2006 | Shadduck |
| 7,018,376 B2 | 3/2006 | Webb et al. |
| 7,094,225 B2 | 8/2006 | Tu et al. |
| 7,125,119 B2 | 10/2006 | Farberov |
| 7,133,137 B2 | 11/2006 | Shimmick |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,488,303 B1 | 2/2009 | Haffner et al. |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | McKenzie et al. |
| 8,012,115 B2 | 9/2011 | Karageozian |
| 8,123,729 B2 | 2/2012 | Yamamoto et al. |
| 8,172,899 B2 | 5/2012 | Silvestrini et al. |
| 8,267,882 B2 | 9/2012 | Euteneuer et al. |
| 8,282,592 B2 | 10/2012 | Schieber et al. |
| 8,337,509 B2 | 12/2012 | Schieber et al. |
| 8,372,026 B2 | 2/2013 | Schieber et al. |
| 8,414,518 B2 | 4/2013 | Schieber et al. |
| 8,425,449 B2 * | 4/2013 | Wardle et al. .................... 604/8 |
| 8,475,374 B2 | 7/2013 | Irazoqui et al. |
| 8,512,404 B2 | 8/2013 | Frion et al. |
| 8,529,494 B2 | 9/2013 | Euteneuer et al. |
| 8,540,659 B2 | 9/2013 | Berlin |
| 8,551,166 B2 | 10/2013 | Schieber et al. |
| 8,629,161 B2 | 1/2014 | Mizuno et al. |
| 8,636,647 B2 | 1/2014 | Silvestrini et al. |
| 8,647,659 B2 | 2/2014 | Robinson et al. |
| 8,657,776 B2 | 2/2014 | Wardle et al. |
| 8,663,150 B2 | 3/2014 | Wardle et al. |
| 8,734,377 B2 | 5/2014 | Schieber et al. |
| 8,808,222 B2 | 8/2014 | Schieber et al. |
| 8,939,948 B2 | 1/2015 | De Juan, Jr. et al. |
| 8,945,038 B2 | 2/2015 | Yablonski |
| 8,951,221 B2 | 2/2015 | Stegmann et al. |
| 8,961,447 B2 | 2/2015 | Schieber et al. |
| 9,039,650 B2 | 5/2015 | Schieber et al. |
| 9,050,169 B2 | 6/2015 | Schieber et al. |
| 9,066,750 B2 | 6/2015 | Wardle et al. |
| 9,066,783 B2 | 6/2015 | Euteneuer et al. |
| 9,155,655 B2 | 10/2015 | Wardle et al. |
| 9,211,213 B2 | 12/2015 | Wardle et al. |
| 9,226,852 B2 | 1/2016 | Schieber et al. |
| 9,636,254 B2 | 5/2017 | Yu et al. |
| 9,642,746 B2 | 5/2017 | Berlin |
| 9,693,901 B2 | 7/2017 | Horvath et al. |
| 9,775,729 B2 | 10/2017 | McClain et al. |
| 9,820,883 B2 | 11/2017 | Berlin |
| 9,833,357 B2 | 12/2017 | Berlin |
| 2001/0002438 A1 | 5/2001 | Sepetka et al. |
| 2002/0003546 A1 | 1/2002 | Mochimaru et al. |
| 2002/0013546 A1 | 1/2002 | Grieshaber et al. |
| 2002/0013572 A1 | 1/2002 | Berlin |
| 2002/0052653 A1 | 5/2002 | Durgin |
| 2002/0072673 A1 | 6/2002 | Yamamoto et al. |
| 2002/0082591 A1 | 6/2002 | Haefliger |
| 2002/0133168 A1 | 9/2002 | Smedley et al. |
| 2002/0143284 A1 | 10/2002 | Tu et al. |
| 2002/0165504 A1 | 11/2002 | Sharp et al. |
| 2002/0165522 A1 | 11/2002 | Holmen |
| 2002/0193805 A1 | 12/2002 | Ott et al. |
| 2003/0004457 A1 | 1/2003 | Andersson |
| 2003/0014092 A1 | 1/2003 | Neuhann |
| 2003/0040754 A1 | 2/2003 | Mitchell et al. |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0060784 A1 | 3/2003 | Hilgers et al. |
| 2003/0093084 A1 | 5/2003 | Nissan et al. |
| 2003/0097151 A1 | 5/2003 | Smedley et al. |
| 2003/0105456 A1 | 6/2003 | Lin |
| 2003/0125351 A1 | 7/2003 | Azuma et al. |
| 2003/0175324 A1 | 9/2003 | Robinson et al. |
| 2003/0181848 A1 | 9/2003 | Bergheim et al. |
| 2003/0187384 A1 | 10/2003 | Bergheim et al. |
| 2003/0212387 A1 | 11/2003 | Kurtz et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0030302 A1 | 2/2004 | Kamata et al. |
| 2004/0070761 A1 | 4/2004 | Horvath et al. |
| 2004/0082939 A1 | 4/2004 | Berlin |
| 2004/0088048 A1 | 5/2004 | Richter et al. |
| 2004/0092856 A1 | 5/2004 | Dahan |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0116909 A1 | 6/2004 | Neuberger et al. |
| 2004/0122380 A1 | 6/2004 | Utterberg |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0199149 A1 | 10/2004 | Myers et al. |
| 2004/0199171 A1 | 10/2004 | Akahoshi |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0228013 A1 | 11/2004 | Goldstein et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |
| 2005/0043722 A1 | 2/2005 | Lin |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0131514 A1 | 6/2005 | Hijlkema et al. |
| 2005/0149114 A1 | 7/2005 | Cartledge et al. |
| 2005/0154443 A1 | 7/2005 | Linder et al. |
| 2005/0165385 A1 | 7/2005 | Simon |
| 2005/0192527 A1 | 9/2005 | Gharib et al. |

(56) References Cited

U.S. PATENT DOCUMENTS

| | | |
|---|---|---|
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0240168 A1 | 10/2005 | Neuberger et al. |
| 2005/0244464 A1 | 11/2005 | Hughes |
| 2005/0245916 A1 | 11/2005 | Connor |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0279369 A1 | 12/2005 | Lin |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0021623 A1 | 2/2006 | Miller et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0084954 A1 | 4/2006 | Zadoyan et al. |
| 2006/0106370 A1 | 5/2006 | Baervekit et al. |
| 2006/0110428 A1 | 5/2006 | deJuan et al. |
| 2006/0116626 A1 | 6/2006 | Smedley et al. |
| 2006/0129141 A1 | 6/2006 | Lin |
| 2006/0149194 A1 | 7/2006 | Conston et al. |
| 2006/0154981 A1 | 7/2006 | Klimko et al. |
| 2006/0155238 A1 | 7/2006 | Shields |
| 2006/0155265 A1 | 7/2006 | Juhasz et al. |
| 2006/0155300 A1 | 7/2006 | Stamper et al. |
| 2006/0167421 A1 | 7/2006 | Quinn |
| 2006/0167466 A1 | 7/2006 | Dusek |
| 2006/0173397 A1 | 8/2006 | Tu et al. |
| 2006/0178674 A1 | 8/2006 | McIntyre |
| 2006/0189915 A1 | 8/2006 | Camras et al. |
| 2006/0189916 A1 | 8/2006 | Bas et al. |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0224146 A1 | 10/2006 | Lin |
| 2006/0241749 A1 | 10/2006 | Tu et al. |
| 2006/0259021 A1 | 11/2006 | Lin |
| 2006/0264971 A1 | 11/2006 | Akahoshi |
| 2006/0276759 A1 | 12/2006 | Kinast et al. |
| 2007/0010827 A1 | 1/2007 | Tu et al. |
| 2007/0021725 A1 | 1/2007 | Villette |
| 2007/0027452 A1 | 2/2007 | Varner et al. |
| 2007/0073275 A1 | 3/2007 | Conston et al. |
| 2007/0088432 A1 | 4/2007 | Solovay et al. |
| 2007/0093794 A1 | 4/2007 | Wang et al. |
| 2007/0093796 A1 | 4/2007 | Raksi et al. |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0121120 A1 | 5/2007 | Schachar |
| 2007/0135681 A1 | 6/2007 | Chin et al. |
| 2007/0173791 A1 | 7/2007 | Raksi |
| 2007/0179520 A1 | 8/2007 | West |
| 2007/0191863 A1 | 8/2007 | De Juan, Jr. et al. |
| 2007/0202186 A1 | 8/2007 | Yamamoto et al. |
| 2007/0208325 A1 | 9/2007 | Kurtz |
| 2007/0219509 A1 | 9/2007 | Tashiro et al. |
| 2007/0219541 A1 | 9/2007 | Kurtz |
| 2007/0235543 A1 | 10/2007 | Zadoyan et al. |
| 2007/0236771 A1 | 10/2007 | Zadoyan et al. |
| 2007/0265582 A1 | 11/2007 | Kaplan et al. |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0293872 A1 | 12/2007 | Peyman |
| 2007/0298068 A1 | 12/2007 | Badawi et al. |
| 2008/0015488 A1 | 1/2008 | Tu et al. |
| 2008/0027519 A1 | 1/2008 | Guerrero |
| 2008/0045878 A1 | 2/2008 | Bergheim et al. |
| 2008/0058704 A1 | 3/2008 | Hee et al. |
| 2008/0058777 A1 | 3/2008 | Kurtz et al. |
| 2008/0082088 A1 | 4/2008 | Kurtz et al. |
| 2008/0091224 A1 | 4/2008 | Griffis et al. |
| 2008/0119827 A1 | 5/2008 | Kurtz et al. |
| 2008/0228127 A1 | 9/2008 | Burns et al. |
| 2008/0278687 A1 | 11/2008 | Somani |
| 2008/0288082 A1 | 11/2008 | Deal |
| 2008/0312661 A1 | 12/2008 | Downer et al. |
| 2009/0005852 A1 | 1/2009 | Gittings et al. |
| 2009/0028953 A1 | 1/2009 | Yamamoto et al. |
| 2009/0030363 A1 | 1/2009 | Gellman |
| 2009/0030381 A1 | 1/2009 | Lind et al. |
| 2009/0036843 A1 | 2/2009 | Erskine |
| 2009/0043321 A1 | 2/2009 | Conston et al. |
| 2009/0054723 A1 | 2/2009 | Khairkhahan et al. |
| 2009/0069786 A1 | 3/2009 | Vesely et al. |
| 2009/0082862 A1 | 3/2009 | Schieber et al. |
| 2009/0104248 A1 | 4/2009 | Rapacki et al. |
| 2009/0118716 A1 | 5/2009 | Brownell |
| 2009/0118717 A1 | 5/2009 | Brownell et al. |
| 2009/0118718 A1 | 5/2009 | Raksi et al. |
| 2009/0131921 A1 | 5/2009 | Kurtz et al. |
| 2009/0137988 A1 | 5/2009 | Kurtz |
| 2009/0138081 A1 | 5/2009 | Bergheim et al. |
| 2009/0157062 A1 | 6/2009 | Hauger et al. |
| 2009/0171327 A1 | 7/2009 | Kurtz et al. |
| 2009/0182421 A1 | 7/2009 | Silvestrini et al. |
| 2009/0198248 A1 | 8/2009 | Yeung et al. |
| 2009/0204053 A1 | 8/2009 | Nissan et al. |
| 2009/0247955 A1 | 10/2009 | Yamamoto et al. |
| 2009/0259126 A1 | 10/2009 | Saal et al. |
| 2009/0281520 A1 | 11/2009 | Highley et al. |
| 2009/0281530 A1 | 11/2009 | Korn |
| 2010/0004580 A1 | 1/2010 | Lynch et al. |
| 2010/0036488 A1 | 2/2010 | de Juan et al. |
| 2010/0057072 A1 | 3/2010 | Roman et al. |
| 2010/0114309 A1 | 5/2010 | de Juan et al. |
| 2010/0137981 A1 | 6/2010 | Silvestrini et al. |
| 2010/0173866 A1 | 7/2010 | Hee et al. |
| 2010/0191176 A1 | 7/2010 | Ho et al. |
| 2010/0191177 A1 | 7/2010 | Chang et al. |
| 2010/0234726 A1 | 9/2010 | Sirimanne et al. |
| 2010/0234790 A1 | 9/2010 | Tu et al. |
| 2010/0262174 A1 | 10/2010 | Sretavan et al. |
| 2010/0324543 A1 | 12/2010 | Kurtz et al. |
| 2010/0331858 A1 | 12/2010 | Simaan et al. |
| 2011/0009874 A1 | 1/2011 | Wardle et al. |
| 2011/0028948 A1 | 2/2011 | Raksi et al. |
| 2011/0028949 A1 | 2/2011 | Raksi et al. |
| 2011/0028950 A1 | 2/2011 | Raksi et al. |
| 2011/0028951 A1 | 2/2011 | Raksi et al. |
| 2011/0028952 A1 | 2/2011 | Raksi et al. |
| 2011/0028953 A1 | 2/2011 | Raksi et al. |
| 2011/0028954 A1 | 2/2011 | Raksi et al. |
| 2011/0028955 A1 | 2/2011 | Raksi |
| 2011/0028957 A1 | 2/2011 | Raksi et al. |
| 2011/0028958 A1 | 2/2011 | Raksi et al. |
| 2011/0098809 A1 | 4/2011 | Wardle et al. |
| 2011/0196487 A1 | 8/2011 | Badawi et al. |
| 2011/0218523 A1 | 9/2011 | Robl |
| 2011/0224597 A1 | 9/2011 | Stegmann et al. |
| 2011/0319806 A1 | 12/2011 | Wardle |
| 2012/0010702 A1 | 1/2012 | Stegmann et al. |
| 2012/0022424 A1 | 1/2012 | Yamamoto et al. |
| 2012/0035524 A1 | 2/2012 | Silvestrini |
| 2012/0191064 A1 | 7/2012 | Conston et al. |
| 2013/0150959 A1 | 6/2013 | Schieber et al. |
| 2013/0182223 A1 | 7/2013 | Wardle et al. |
| 2013/0281907 A1 | 10/2013 | Wardle et al. |

(56) References Cited

U.S. PATENT DOCUMENTS

| | | |
|---|---|---|
| 2014/0066821 A1 | 3/2014 | Freidland et al. |
| 2014/0066831 A1 | 3/2014 | Silvestrini et al. |
| 2014/0249463 A1 | 9/2014 | Wardle et al. |
| 2015/0119787 A1 | 4/2015 | Wardle et al. |
| 2015/0223983 A1 | 8/2015 | Schieber et al. |
| 2015/0223985 A1 | 8/2015 | Schieber et al. |
| 2015/0250649 A1 | 9/2015 | Euteneuer et al. |
| 2015/0282982 A1 | 10/2015 | Schieber et al. |
| 2015/0290033 A1 | 10/2015 | Wardle et al. |
| 2015/0366710 A1 | 12/2015 | Schieber et al. |
| 2017/0143541 A1 | 5/2017 | Badawi et al. |
| 2017/0172794 A1 | 6/2017 | Varner et al. |
| 2017/0202708 A1 | 7/2017 | Berlin |
| 2017/0239272 A1 | 8/2017 | Ambati et al. |
| 2017/0281409 A1 | 10/2017 | Haffner et al. |
| 2017/0290705 A1 | 10/2017 | Wardle et al. |
| 2018/0221205 A1 | 8/2018 | Berlin |

FOREIGN PATENT DOCUMENTS

| | | |
|---|---|---|
| DE | 4226476 C1 | 8/1993 |
| EP | 0168201 B1 | 6/1988 |
| EP | 0957949 A1 | 11/1996 |
| EP | 0766544 B1 | 5/1998 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| EP | 1732484 B1 | 8/2017 |
| EP | 1740153 B2 | 8/2017 |
| EP | 3205333 A1 | 8/2017 |
| JP | H10-504978 A | 5/1998 |
| JP | 11123205 | 5/1999 |
| JP | 2002542872 | 12/2002 |
| JP | 2006517848 | 8/2006 |
| JP | 2006289075 A | 10/2006 |
| JP | 2010509003 | 3/2010 |
| JP | 2011502649 | 1/2011 |
| WO | WO96/20742 A1 | 7/1996 |
| WO | WO99/01063 A1 | 1/1999 |
| WO | WO99/45868 A1 | 9/1999 |
| WO | WO 00/07525 A1 | 2/2000 |
| WO | WO00/13627 A1 | 3/2000 |
| WO | WO 00/64389 A1 | 11/2000 |
| WO | WO 00/64393 A1 | 11/2000 |
| WO | WO00/67687 A1 | 11/2000 |
| WO | WO01/89437 A2 | 11/2001 |
| WO | WO 01/97727 A1 | 12/2001 |
| WO | WO 02/36052 A1 | 5/2002 |
| WO | WO 02/074052 A2 | 9/2002 |
| WO | WO 02/080811 A2 | 10/2002 |
| WO | WO 03/015659 A2 | 2/2003 |
| WO | WO 03/045290 A1 | 6/2003 |
| WO | WO 2004/054643 A1 | 7/2004 |
| WO | WO 2004/093761 A1 | 11/2004 |
| WO | WO 2005/105197 A2 | 11/2005 |
| WO | WO 2006/066103 A2 | 6/2006 |
| WO | WO 2007/035356 A2 | 3/2007 |
| WO | WO 2007/047744 A2 | 4/2007 |
| WO | WO 2007/087061 A2 | 8/2007 |
| WO | WO 2008/002377 A1 | 1/2008 |
| WO | WO 2008/005873 A2 | 1/2008 |
| WO | WO 2009/042596 A2 | 4/2009 |
| WO | WO 2009/120960 A2 | 10/2009 |
| WO | WO 2011/053512 A1 | 5/2011 |
| WO | WO 2011/057283 A1 | 5/2011 |
| WO | WO 2011/106781 A1 | 9/2011 |
| WO | WO 2011/150045 A1 | 12/2011 |

OTHER PUBLICATIONS

D'Ermo, et al.; Our results with the operation of ab externo trabeculotomy; Ophthalmologica; vol. 163; pp. 347-355; Feb. 1971.
Ellingsen et al.; Trabeculotomy and sinusotomy in enucleated human eyes; Investigative Ophthalmology; vol. 11; pp. 21-28; Jan. 1972.
Grant; Experimental aqueous perfusion in enucleated human eyes; Archives of Ophthalmology; vol. 69; pp. 783-801; Jun. 1963.
Johnstone et al.; "Microsurgery of Schlemm's Canal and the Human Aqueous Outflow System;" American Journal of Ophthalmology, vol. 76 (6): 906-917; Dec. 1973.
Lee et al.; Aqueous-venous shunt and intraocular pressure. Preliminary report of animal studies; Investigative Ophthalmology; vol. 5; No. 1; pp. 59-64; Feb. 1966.
Lynch, Mary G.; U.S. Appl. No. 60/131,030 entitled "Devices and methods for treating glaucoma by enhancing aqueous outflow through schlemm's canal and anterior chamber angle ," filed Apr. 26, 1999.
Moses, Robert; The effect of intraocular pressure on resistance to outflow; Survey of Ophthalmology; vol. 22; No. 2; pp. 88-100; Sep.-Oct. 1977.
Mäepea et al.; The pressures in the episcleral veins, schlemm's canal and the trabecular meshwork in monkeys: effects of changes in intraocular pressure; Exp. Eye Res.; vol. 49; pp. 645-663; Oct. 1989.
Rosenquist et al.; Outflow resistance of enucleated human eyes at two different perfusion pressures and different extents of trabeculotomy; Current Eye Res.; vol. 8; No. 12; pp. 1233-1240; Dec. 1989.
Savage, James; Gonioscopy in the management of glaucoma; Am. Academy of Ophthalmology; Focal Points; vol. XXIV; No. 3; pp. 1-14; Mar. 2006.
Schultz, Jared; Canaloplasty procedure shows promise for open-angle glaucoma in European study; Ocular Surgery News; vol. 34; Mar. 1, 2007.
Smit et al.; Effects of viscoelastic injection into schlemm's canal in primate and human eyes; J. Am. Academy of Ophthalmology; vol. 109; No. 4; pp. 786-792; Apr. 2002.
Spiegel et al.; Schlemm's canal implant: a new method to lower intraocular pressure in patients with POAG?; Ophthalmic Surgery and Lasers; vol. 30; No. 6; pp. 492-494; Jun. 1999.
Euteneuer et al.; U.S. Appl. No. 15/601,756 entitled "Methods and apparatus for treating glaucoma," filed May 22, 2017.
Kirkness et al.; The Use of Silicone Drainage Tubing to Control Post-Keratoplasty Glaucoma; Eye; 2 (pt 5); pp. 583-590; Apr. 1988.
Molteno et al.; Long Tube Implants in the Management of Glaucoma; SA Medical Journal; 26; pp. 1062-1066; Jun. 1976.
Molteno; New implant for drainage in glaucoma; Brit. J. Ophthal; 53; pp. 606-615; Sep. 1969.
Schocket et al.; Anterior Chamber Tube Shunt to an Encircling Band in the Treatment of Neovascular Glaucoma and other Refractory Glaucomas; Ophthalmology; 92; pp. 553-562; Apr. 1985.
Wilcox et al.; Hypothesis for Improving Accessory Filtration by Using Geometry; Journal of Glaucoma; 3; pp. 244-247; Fall 1994.
Schieber; U.S. Appl. No. 15/325,628 entitled "Ocular implant delivery system and method," filed Jan. 11, 2017.
Schieber et al.; U.S. Appl. No. 15/012,544 entitled "Methods and devices for increasing aqueous humor outflow," filed Feb. 1, 2016.
Wardle et al.; U.S. Appl. No. 15/150,175 entitled "Ocular implants for delivery into an anterior chamber of the eye," filed May 9, 2016.
Berlin et al.; U.S. Appl. No. 15/868,904 entitled Methods and systems for OCT guided glaucoma surgery, filed Jan. 11, 2018.
Cambridge Dictionary; Sensor (definition); 2 pages; retrived from the internet (http://dictionary.cambridge.org/define.asp?dict=CALD &key=71811 >) on Aug. 14, 2018.
Dietlein et al.; Morphological variability of the trabecular meshwork in glaucoma patients: implications for non-perforating glaucoma surgery; British Journal of Ophthalmology; 84(12); pp. 1354-1359; Dec. 2000.
Huang et al.; Optical coherence tomography; Science; 254(5035); pp. 1178-1181; 12 pages (Author Manuscript); Nov. 1991.
Johnstone; Aqueous humor outflow system overview; Becker-Shaffer's Diagnosis and Therapy of the Glaucomas; Part 2 Aqueous

(56) References Cited

OTHER PUBLICATIONS

Humor Dynamics; Chapter 3; pp. 25-46; Mosby Elseveir; (year of pub. sufficiently earlier than effective US filing date and any foreign priority date) 2009.

Lee et al.; Short-pulsed neodymium-YAG laser trabeculotomy. An in vivo morphological study in the human eye; Investigative Ophthalmology and Visual Science; 29(11); pp. 1698-1707; Nov. 1988.

Toyran et al.; Femtosecond laser photodisruption of human trabecular meshwork: an in vitro study; Experimental Eye Research; 81(3); pp. 298-305; Sep. 2005.

Macmilla Online Dictionary; Detector (definition); Macmilla On Line Dictionary; 2 pages; retrived from the internet (https://www.macmillandictionary.com/dictionary/british/detector) on Aug. 14, 2018.

Nakamura et al.; Femtosecond laser photodisruption of primate trabecular meshwork: an ex vivo study; Investigative Ophthalmology and Visual Science; 50(3); pp. 1198-1204; Mar. 2009.

Owen; A moving-mirror gonioscope for retinal surgery; British Journal of Ophthalmology; 61(3); pp. 246-247; Mar. 1977.

Oxford Dictionaries; Detector (definition); 1 page; retrieved from the internet (https://en.oxforddictionaries.com/definition/detector) on Aug. 14, 2018.

Oxford Dictionaries; Sensor (definition); 1 page; retrieved from to internet (http://wvvw.askoxford.com/concise_oed/sensor?view=uk>) on Aug. 14, 2018.

Radhakrishnan et al.; Real-time optical coherence tomography of the anterior segment at 1310 nm; Archives of Opthhalmology; 119(8); pp. 1179-1185; Aug. 2001.

Van Meter et al.; U.S. Appl. No. 15/751,886 entitled "Ocular implant with pressure sensor and delivery system," filed Feb. 12, 2018.

\* cited by examiner

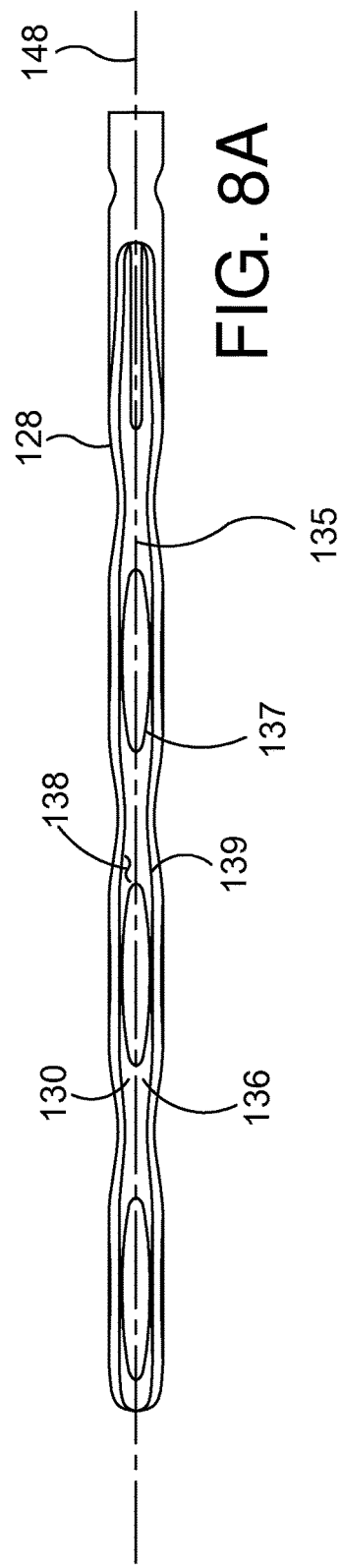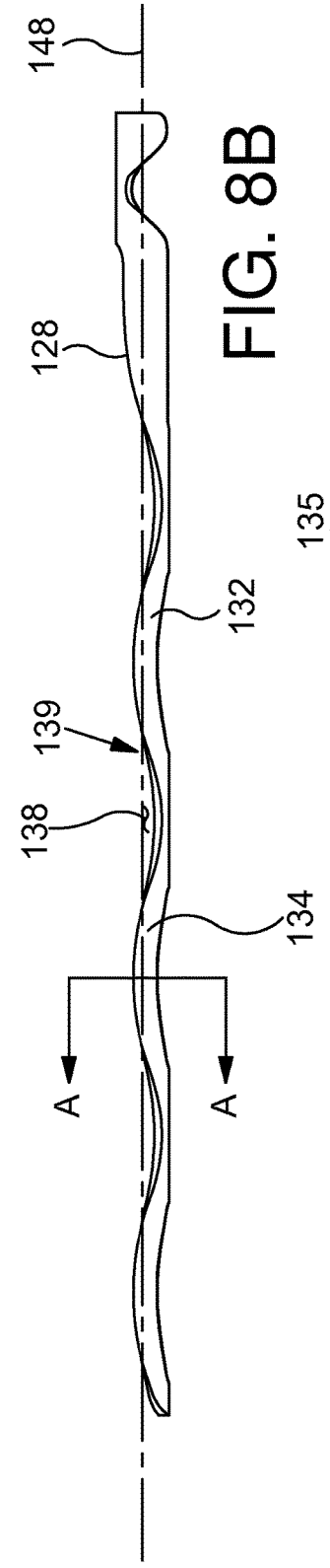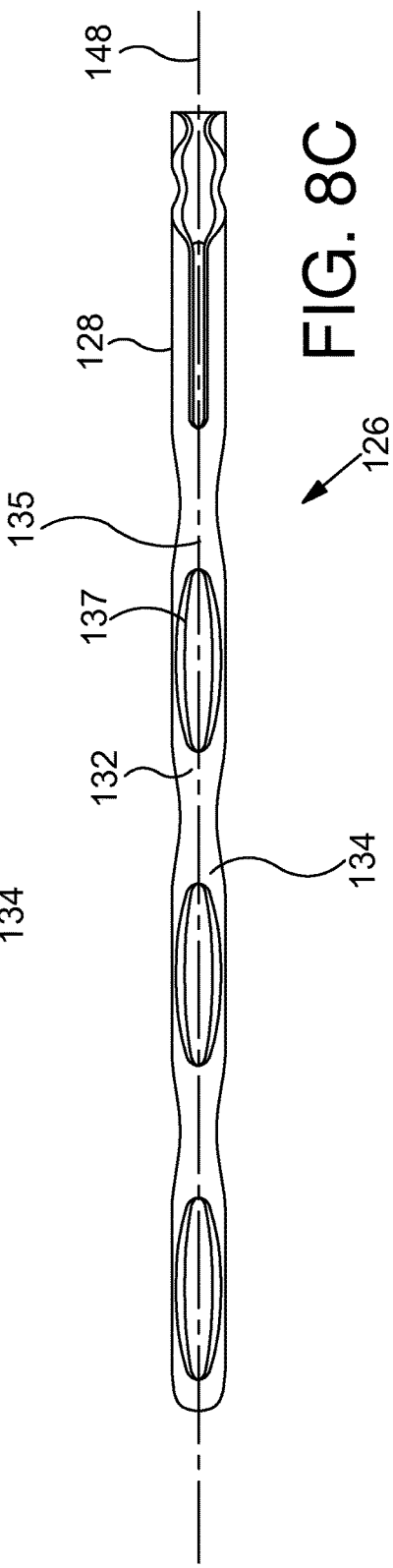

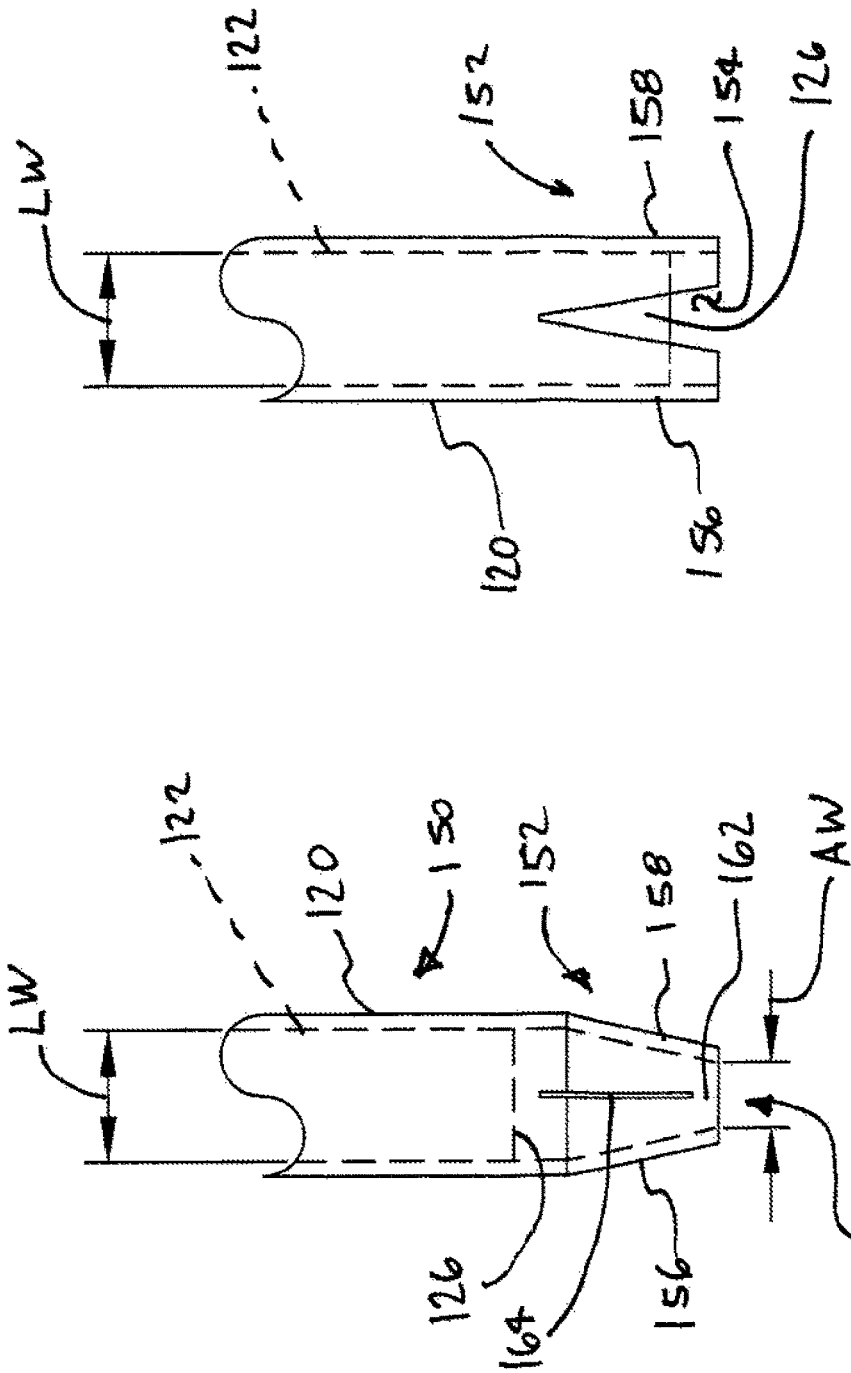

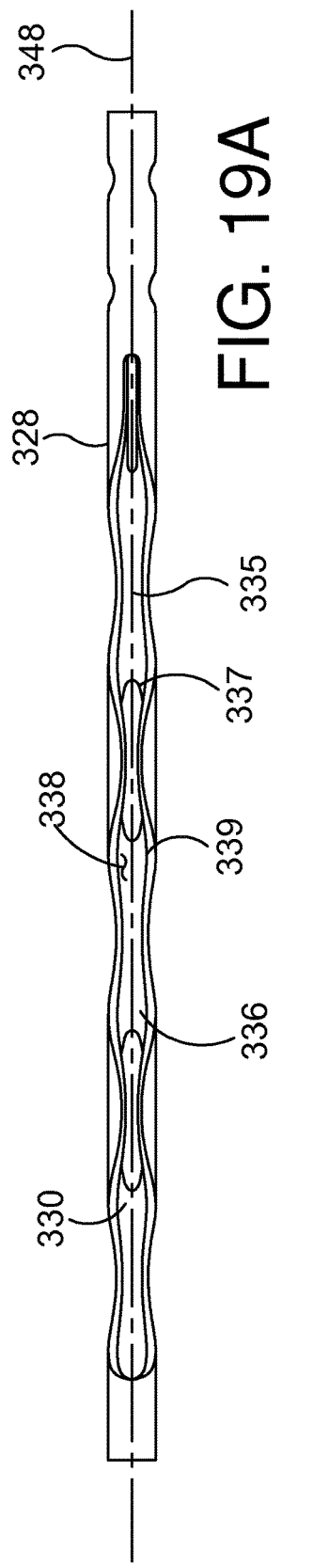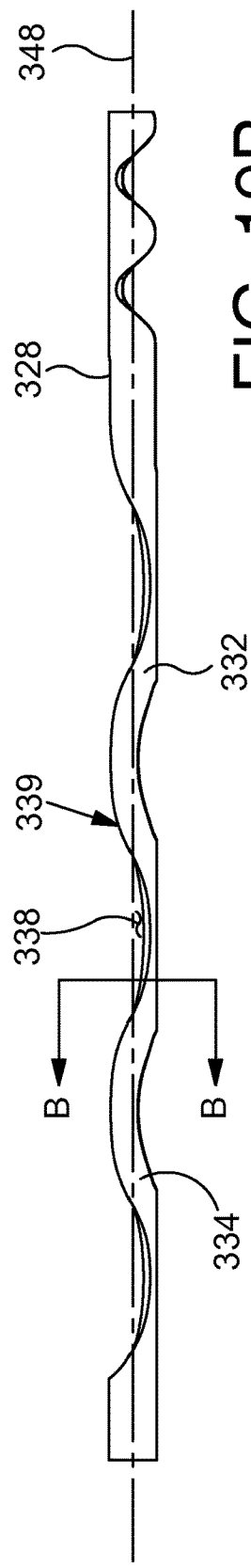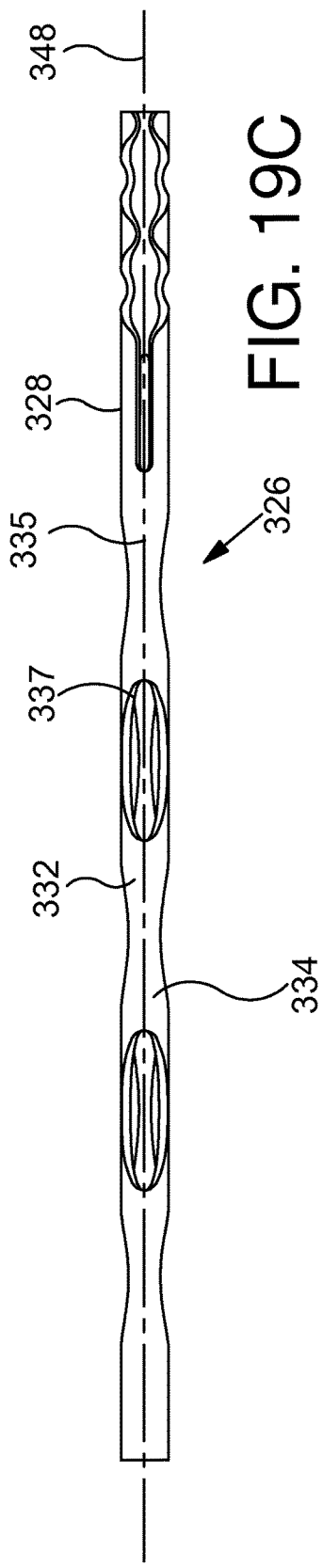

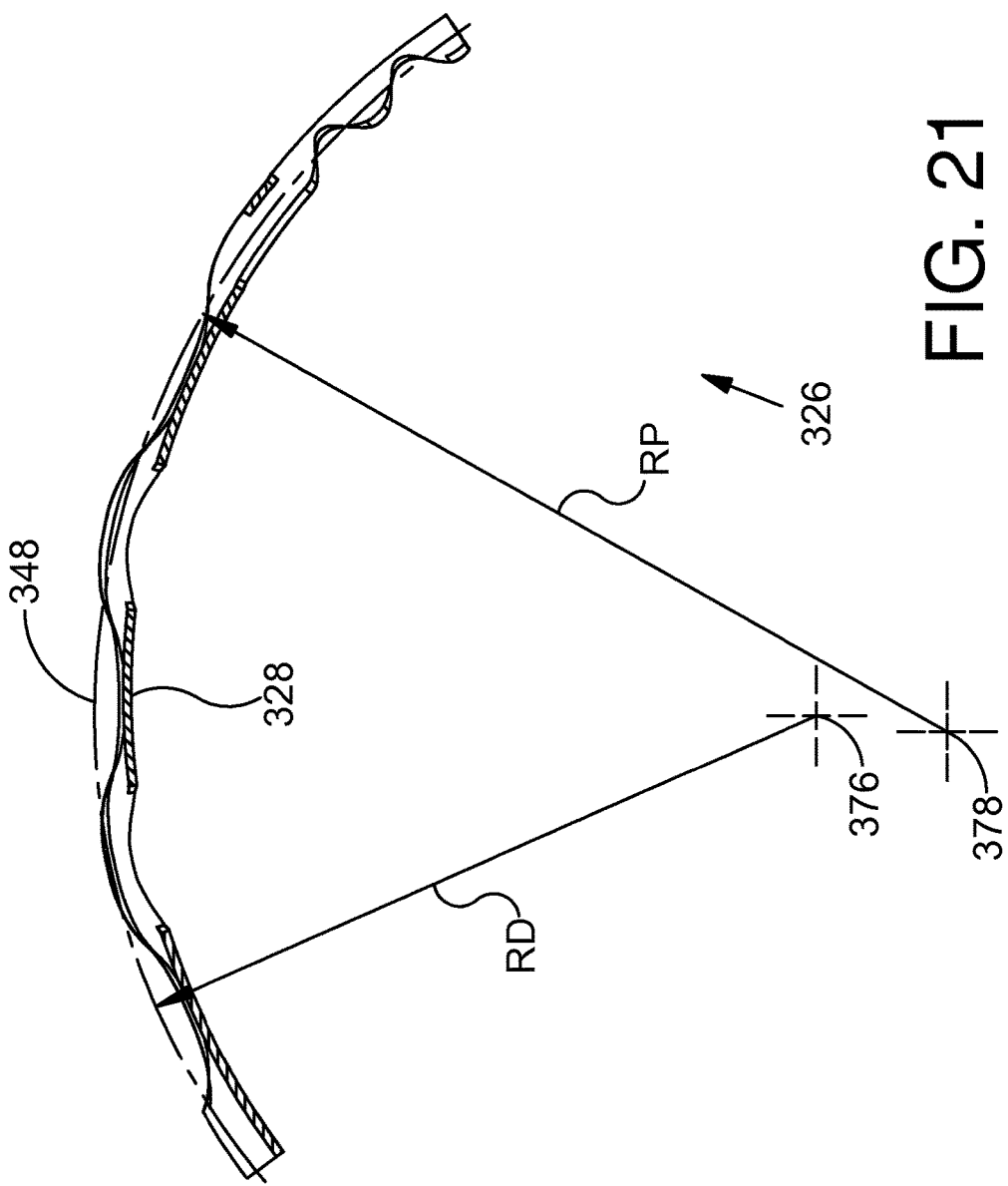

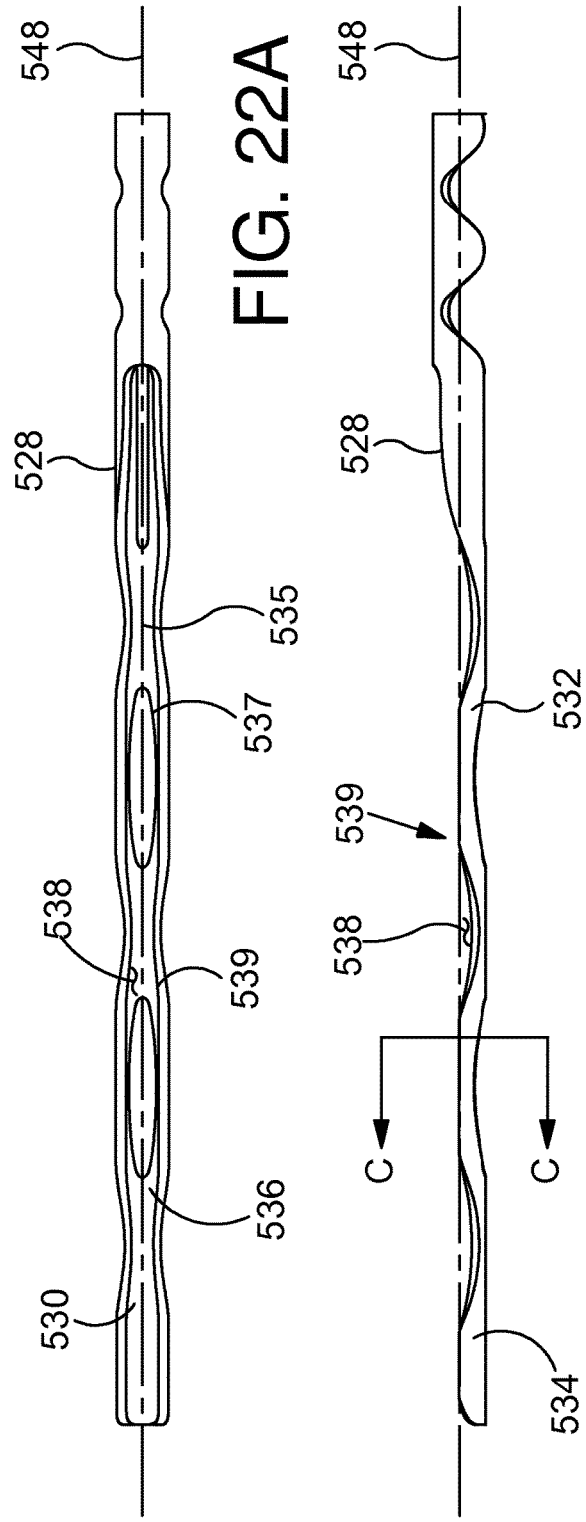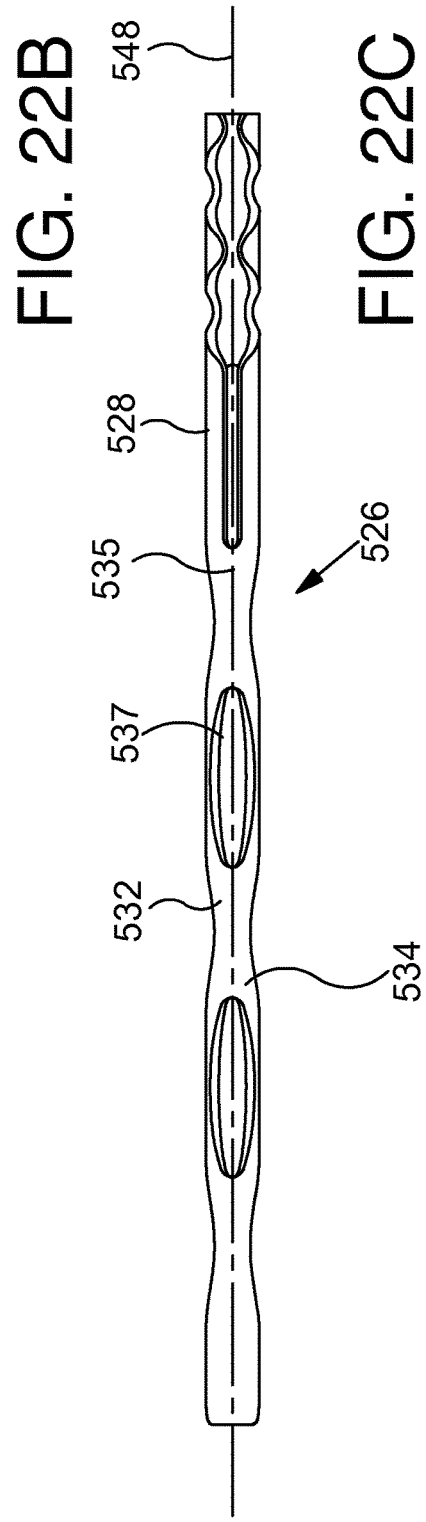

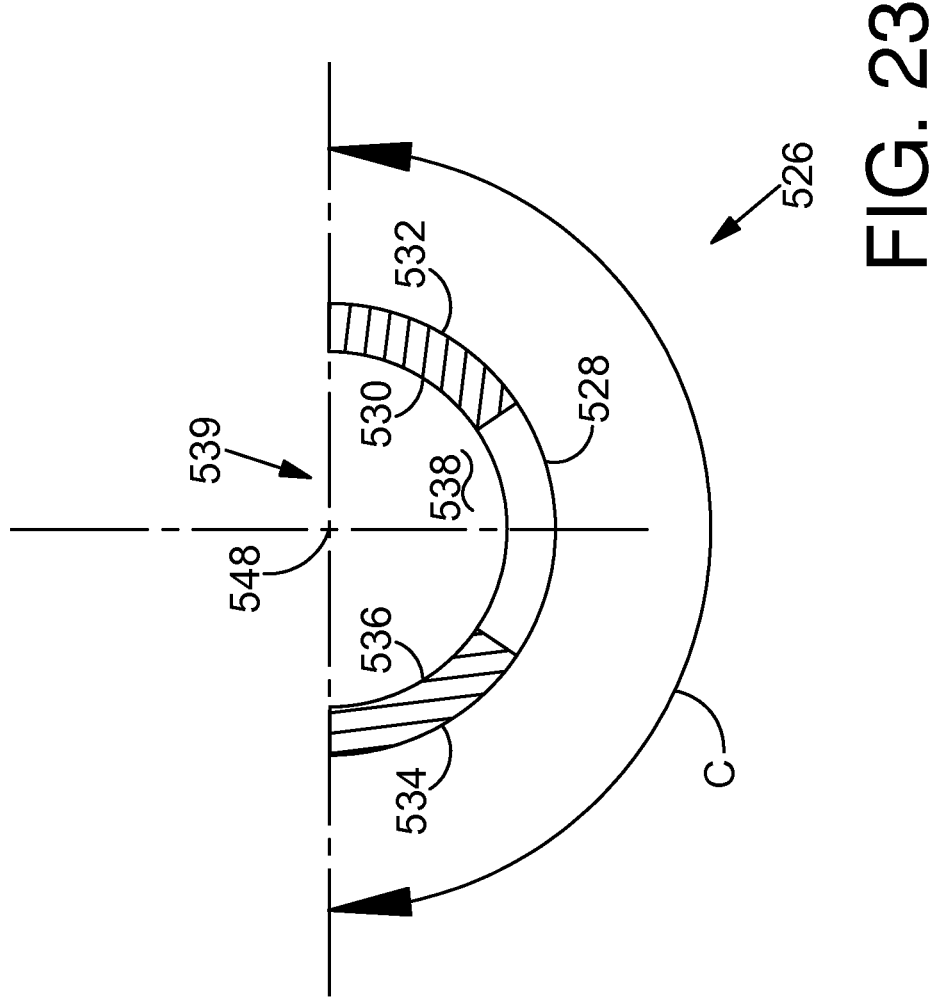

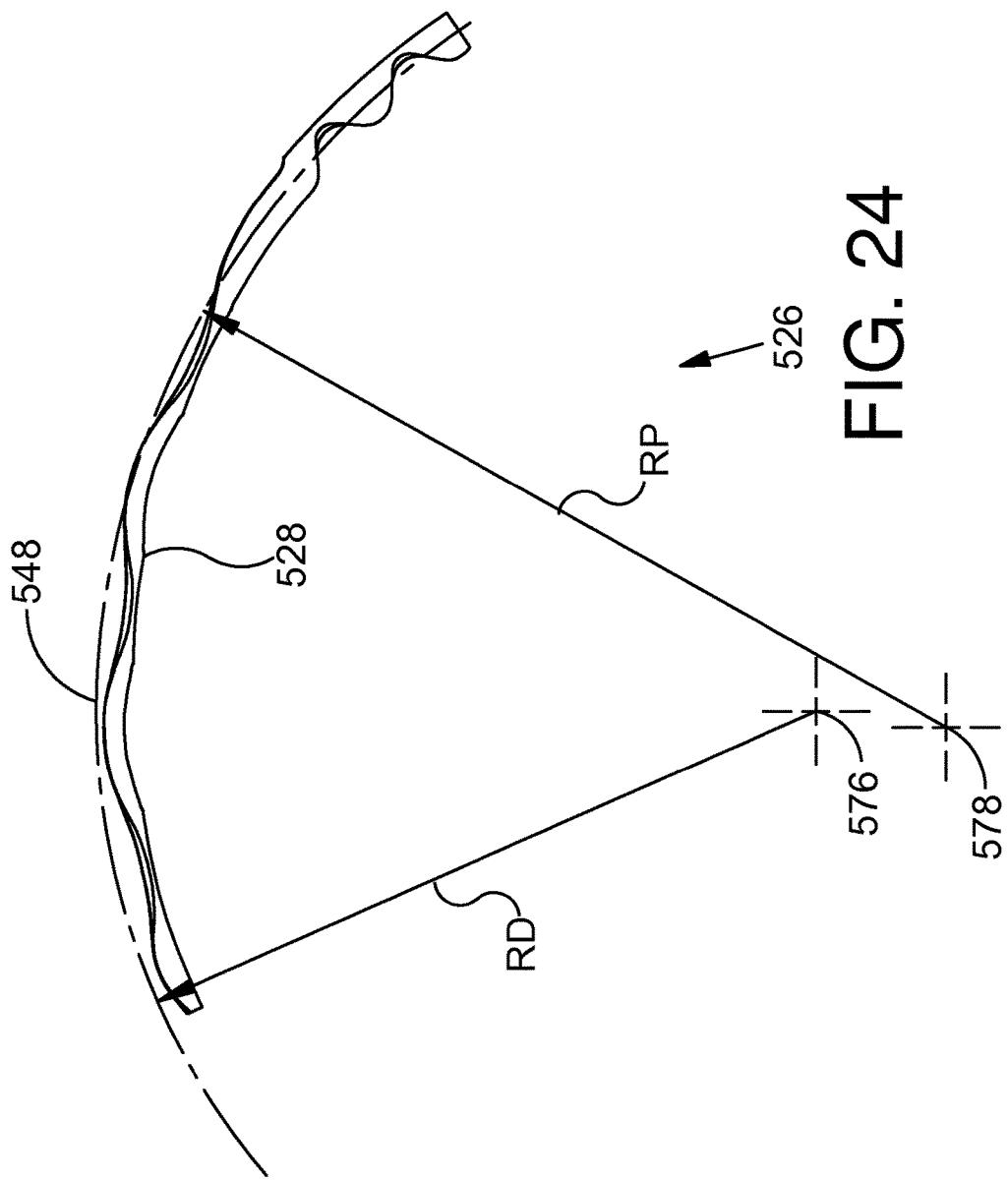

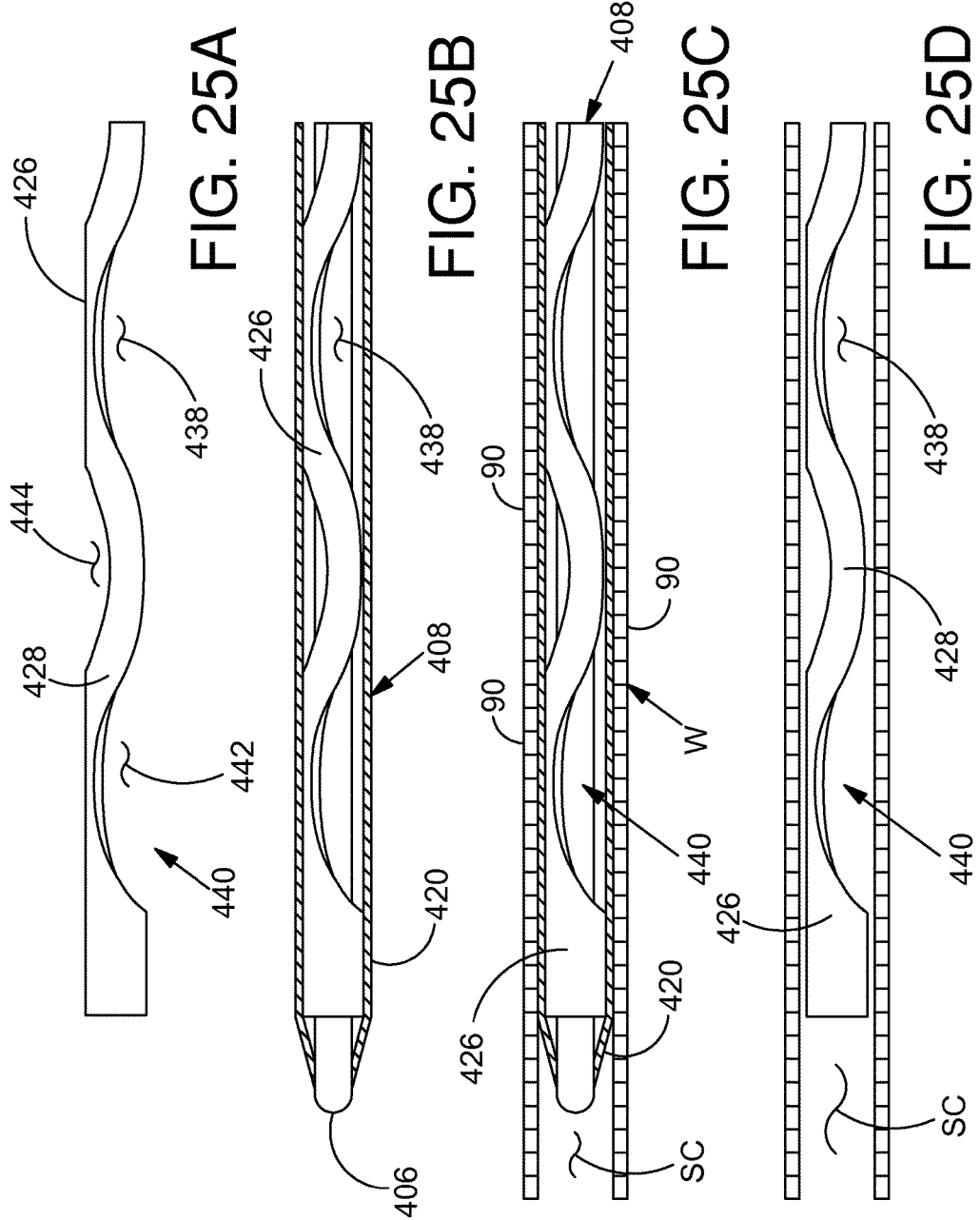

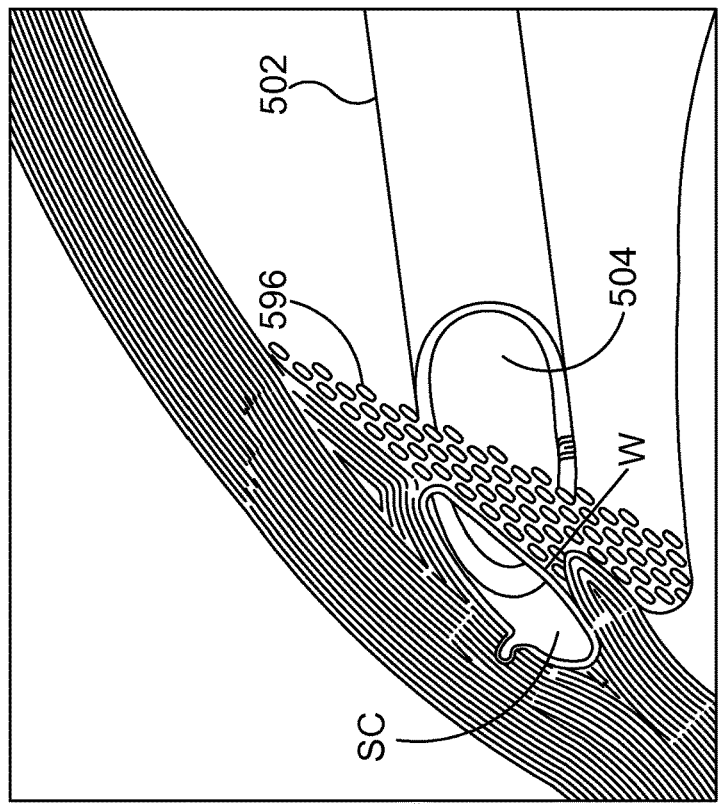
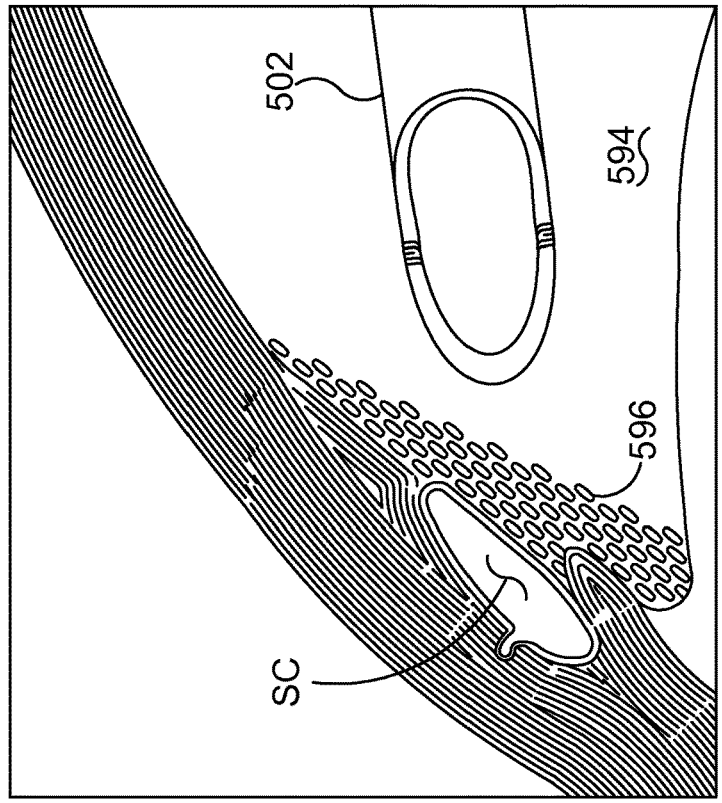

OCULAR IMPLANTS AND METHODS FOR DELIVERING OCULAR IMPLANTS INTO THE EYE

CROSS REFERENCE TO RELATED APPLICATIONS

This application is a continuation of U.S. application Ser. No. 13/865,770, filed Apr. 18, 2013, which application is a continuation of U.S. application Ser. No. 12/833,863, filed Jul. 9, 2010, now U.S. Pat. No. 8,425,449, which application claims the benefit under 35 U.S.C. 119 of U.S. Provisional Application No. 61/224,158, filed Jul. 9, 2009, titled "Sheathed Ocular Implant and Delivery System". These applications are herein incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to devices that are implanted within the eye. More particularly, the present invention relates to systems, devices and methods for delivering ocular implants into the eye.

BACKGROUND OF THE INVENTION

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," *Investigative Ophthalmology* (February 1966)). Other early glaucoma treatment implants led from the anterior chamber to a sub-conjunctival bleb (e.g., U.S. Pat. Nos. 4,968,296 and 5,180,362). Still others were shunts leading from the anterior chamber to a point just inside Schlemm's canal (Spiegel et al., "Schlemm's canal implant: a new method to lower intraocular pressure in patients with POAG?" *Ophthalmic Surgery and Lasers* (June 1999); U.S. Pat. Nos. 6,450,984; 6,450,984).

SUMMARY OF THE DISCLOSURE

The invention pertains to aspects of ocular implants, ocular implant delivery systems, and methods for delivering ocular implants. One aspect of the invention an ocular implant adapted to reside at least partially in a portion of Schlemm's canal of an eye. In some embodiments, the ocular implant includes a body having a first major surface and a second major surface, the body being curved about a longitudinal central axis so that the first major surface comprises a concave surface and the second major surface comprises a convex surface, a distal portion of the body defining a longitudinal channel including a channel opening, the channel opening being disposed diametrically opposite a central portion of the concave surface, and the body being adapted and configured such that the ocular implant assumes an orientation in which the channel opening is adjacent a major side of Schlemm's canal when the ocular implant is disposed in Schlemm's canal. The channel may opens away from the pupil of the when the channel opening is adjacent an outer major side of Schlemm's canal.

In some embodiments, the channel has a width and a depth and an aspect ratio of the width to the depth is such that the ocular implant assumes an orientation in which the channel opening is adjacent a major side of Schlemm's canal when the ocular implant is disposed in Schlemm's canal. In some useful embodiments, the aspect ratio of channel width WD to channel depth DP is greater than about one. In some particularly useful embodiments, the aspect ratio of channel width WD to channel depth DP is about two. In some useful embodiments, the aspect ratio of channel width WD to channel depth DP is greater than about two.

In some embodiments, the body has a first lateral extent, a second lateral extent, and a longitudinal length and an aspect ratio of the first lateral extent to the second lateral extent is such that the ocular implant assumes an orientation in which the channel opening is adjacent a major side of Schlemm's canal when the ocular implant is disposed in Schlemm's canal. In some useful embodiments, an aspect ratio of first lateral extent EF to second lateral extent ES is greater than about one. In some particularly useful embodiments, the aspect ratio of first lateral extent EF to second lateral extent ES is about two. In some useful embodiments, the aspect ratio of first lateral extent EF to second lateral extent ES is greater than about two.

In some embodiments, a distal portion of the body of the ocular implant extends across an angular span of less than 180 degrees as the body curves about the longitudinal central axis. In some embodiments, the body defines additional openings fluidly communicating with the channel and the body of the implant is more than 50% open due to the openings defined by the body. In some embodiments, the body of the ocular implant has a diameter of between about 0.005 inches and about 0.04 inches.

In some embodiments, the ocular implant comprises a therapeutic agent deposited on the body. In some of these embodiments, a therapeutic agent comprises an anti-glaucoma drug. The anti-glaucoma drug comprises a prostaglandin analog in some embodiments. The prostaglandin analog comprises latanprost in some embodiments.

In some embodiments, the body of the ocular implant has a thickness extending between the concave surface and the convex surface. The thickness of the body is substantially uniform along a length of the body in some embodiments. In some embodiments, the thickness of the body is substantially uniform along a circumference of the body.

In some embodiments, the body is curved about a lateral central axis so that a longitudinal axis of the body defines a plane. When this is the case, the body has a lateral radius of curvature extending between the lateral central axis and an outer extent of the body. The lateral radius of curvature is substantially constant in some embodiments. In other embodiments, the lateral radius of curvature varies along a length of the body.

Another aspect of the invention provides an ocular implant system for treating an eye. In some embodiments, the ocular implant system comprises a delivery cannula comprising a tubular member defining a distal opening, a proximal opening, and a passageway extending between the proximal opening and the distal opening. In some embodiments, the delivery cannula includes a curved portion disposed between the distal opening and the proximal opening, the delivery cannula being adapted and configured such that the distal opening can be placed in fluid communication with Schlemm's canal when the cannula is extending through the cornea of the eye and the curved portion of the cannula is at least partially disposed in the anterior chamber of the eye. In some embodiments, the implant system includes an ocular implant disposed in the passageway defined by the delivery cannula, the ocular implant comprising a body having a first major surface and a second major surface, the body being curved about a longitudinal central axis so that the first major surface comprises a concave surface and the second major surface comprises a convex surface, a distal portion of the body defining a longitudinal channel including a channel opening. In some useful embodiments, the ocular implant is oriented relative to the delivery cannula such that the channel of the ocular implant opens in a radially outward direction when the ocular implant passes through the curved portion of the delivery cannula.

An additional aspect of the invention provides another ocular implant system for treating an eye. In some embodiments, the ocular implant system comprises an ocular implant defining a plurality of openings and a sheath disposed about the body of the ocular implant. In some embodiments, the sheath covers at least some of the openings and the sheath is adapted and configured such that the sheath can be selectively removed from the body for uncovering the openings.

In some embodiments, the sheath comprises a proximal portion defining a lumen and a distal portion defining a distal aperture, the lumen having a lumen width and the distal aperture having an aperture width. The aperture width is smaller than the lumen width in some embodiments. The distal portion provides a transition from the lumen width to the aperture width in some embodiments. In some embodiments, the lumen width is equal to or greater than a width of the implant and the aperture width is smaller than the width of the implant.

In some embodiments, the distal portion of the sheath comprises a first region, a second region, and a slit disposed between the first region and the second region. The sheath includes a frangible connection between the first region and the second region in some embodiments. In some embodiments, the frangible connection comprises a bridge extending across the slit. The aperture width of the distal aperture may become larger when the frangible connection is broken.

In some embodiments, the distal portion of the sheath has a first hoop strength, the proximal portion of the sheath has a second hoop strength, and the second hoop strength is greater than the first hoop strength. The hoop strength of the distal portion is limited by the frangible connection in some embodiments.

In some embodiments, the distal portion of the sheath extends beyond a distal end of the implant. The frangible connection breaks when the sheath is moved in a proximal direction relative to the implant in some embodiments. The distal portion of the sheath has a tapered shape in some embodiments. In other embodiments, the distal portion of the sheath has a blunt shape.

In some embodiments, the ocular implant system may include a core resting in the longitudinal channel of the implant and a push tube contacting a proximal end of the implant. The core, the push tube, and the sheath extend into a lumen defined by a cannula in some embodiments. The implant may be disposed in a lumen defined by the cannula.

Yet another aspect of the invention provides a method of deploying an ocular implant into Schlemm's canal of a human eye. In some embodiments, the method includes providing an ocular implant comprising a body having a first major surface and a second major surface, the body being curved about a longitudinal central axis so that the first major surface comprises a concave surface and the second major surface comprises a convex surface, a distal portion of the body defining a longitudinal channel including a channel opening, the body defining additional openings fluidly communicating with the channel. The method may include the following steps: covering at least some of the openings; advancing at least a distal portion of the implant into Schlemm's canal while at least some of the openings are covered; and uncovering at least some of the openings while the distal portion of the implant is disposed in Schlemm's canal. In some embodiments, the method includes orienting the ocular implant so that the channel opening is adjacent an outer major side of Schlemm's canal.

In some embodiments, covering at least some of the apertures comprises positioning a sheath over at least a portion of the implant and uncovering at least some of the apertures comprises moving the sheath in a proximal direction relative to the implant. Uncovering at least some of the apertures comprises breaking a frangible portion of the sheath in some embodiments. The frangible portion of the sheath may be broken, for example, when the sheath is moved in a proximal direction relative to the implant. Moving the sheath in a proximal direction relative to the implant may be accomplished by, for example, applying a proximal directed force to the sheath while applying a distally directed reaction force on the implant. Applying a distally directed reaction force on the implant may be accomplished by, for example, pushing on a proximal end of the implant with a push tube.

BRIEF DESCRIPTION OF THE DRAWINGS

FIG. 8A, FIG. 8B and FIG. 8C are multiple plan views illustrating an implant in accordance with the present detailed description.

FIG. 18A and FIG. 18B are simplified plan views showing a sheath in accordance with the present detailed description.

FIG. 19A, FIG. 19B and FIG. 19C are plan views showing an implant in accordance with the present detailed description.

FIG. 21 is a plan view showing an implant in accordance with the present detailed description.

FIG. 22A, FIG. 22B and FIG. 22C are plan views showing an additional implant in accordance with the present detailed description.

FIG. 23 is a lateral cross-sectional view of an ocular implant taken along section line B-B shown in the previous Figure.

FIG. 24 is a plan view showing an implant in accordance with the present detailed description.

FIG. 25A through FIG. 25D are a series of plan views illustrating a method in accordance with the present detailed description.

FIG. 26A through FIG. 26D are a series of section views illustrating a method in accordance with the present detailed description.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
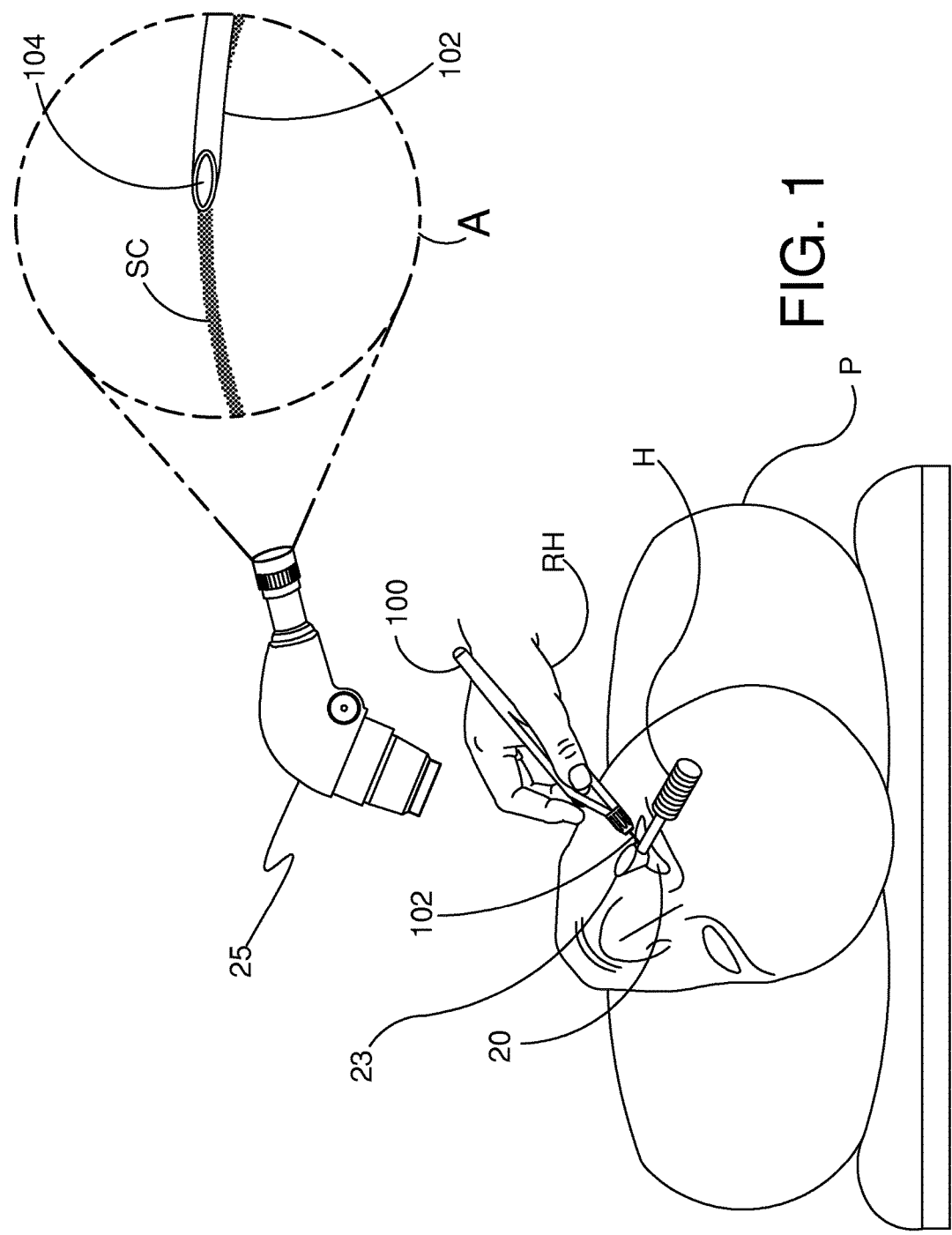
FIG. 1 is a stylized representation of a medical procedure in accordance with this detailed description.

FIG. 1 is a stylized representation of a medical procedure in accordance with this detailed description. In the procedure of FIG. 1, a physician is treating an eye 20 of a patient P. In the procedure of FIG. 1, the physician is holding a delivery system 100 in his or her right hand RH. The physician's left hand (not shown) may be used to hold the handle H of a gonio lens 23. It will be appreciated that some physician's may prefer holding the delivery system handle in the left hand and the gonio lens handle H in the right hand RH.

During the procedure illustrated in FIG. 1, the physician may view the interior of the anterior chamber using gonio lens 23 and a microscope 25. Detail A of FIG. 1 is a stylized simulation of the image viewed by the physician. A distal portion of a cannula 102 is visible in Detail A. A shadow-like line indicates the location of Schlemm's canal SC which is lying under various tissue (e.g., the trabecular meshwork) that surround the anterior chamber. A distal opening 104 of cannula 102 is positioned near Schlemm's canal SC of eye 20. In some methods in accordance with this detailed description, distal opening 104 of cannula 102 is placed in fluid communication with Schlemm's canal SC. When this is the case, an ocular implant may be advanced through distal opening 104 and into Schlemm's canal SC.

Figure 2:
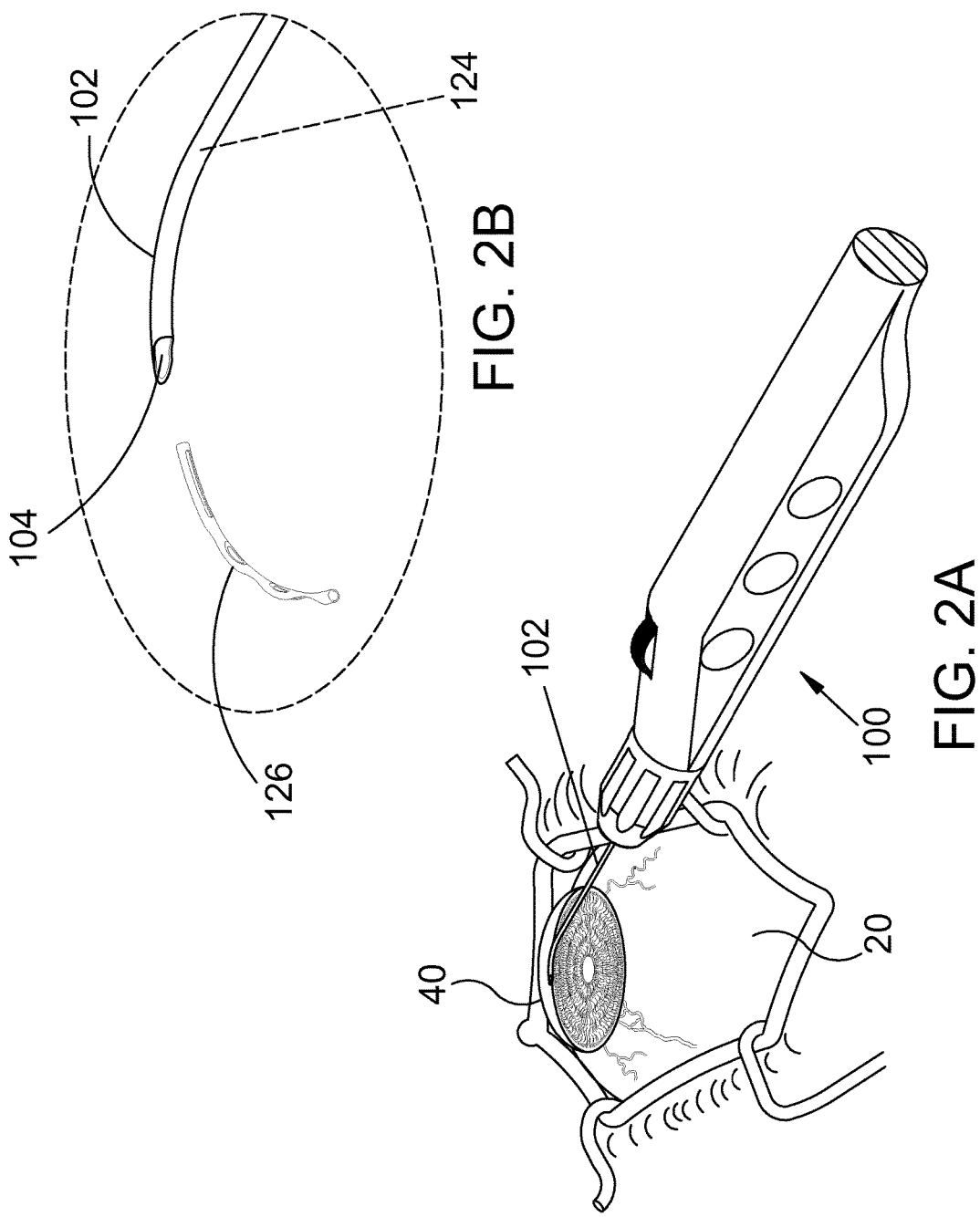
FIG. 2A is a perspective view further illustrating a delivery system 100 used in the medical procedure shown in the previous Figure.
FIG. 2B is an enlarged detail view further illustrating a cannula of the delivery system shown in the previous Figure.

FIG. 2A is a perspective view further illustrating delivery system 100 and eye 20 shown in the previous Figure. In FIG. 2A, cannula 102 of delivery system 100 is shown extending through a cornea 40 of eye 20. A distal portion of cannula 102 is disposed inside the anterior chamber defined by cornea 40 of eye 20. In the embodiment of FIG. 2A, cannula 102 is configured so that a distal opening 104 of cannula 102 can be placed in fluid communication with Schlemm's canal.

In the embodiment of FIG. 2A, an ocular implant is disposed in a lumen defined by cannula 102. Delivery system 100 includes a mechanism that is capable of advancing and retracting the ocular implant along the length of cannula 102. The ocular implant may be placed in Schlemm's canal of eye 20 by advancing the ocular implant through distal opening 104 of cannula 102 while distal opening 104 is in fluid communication with Schlemm's canal.

FIG. 2B is an enlarged detail view further illustrating cannula 102 of delivery system 100. In the illustrative embodiment of FIG. 2B, an ocular implant 126 has been advanced through distal opening 104 of cannula 102. Cannula 102 of FIG. 2B defines a passageway 124 that fluidly communicates with distal opening 104. Ocular implant 126 may be moved along passageway 124 and through distal opening by delivery system 100. Delivery system 100 includes a mechanism capable of performing this function.

Figure 3:
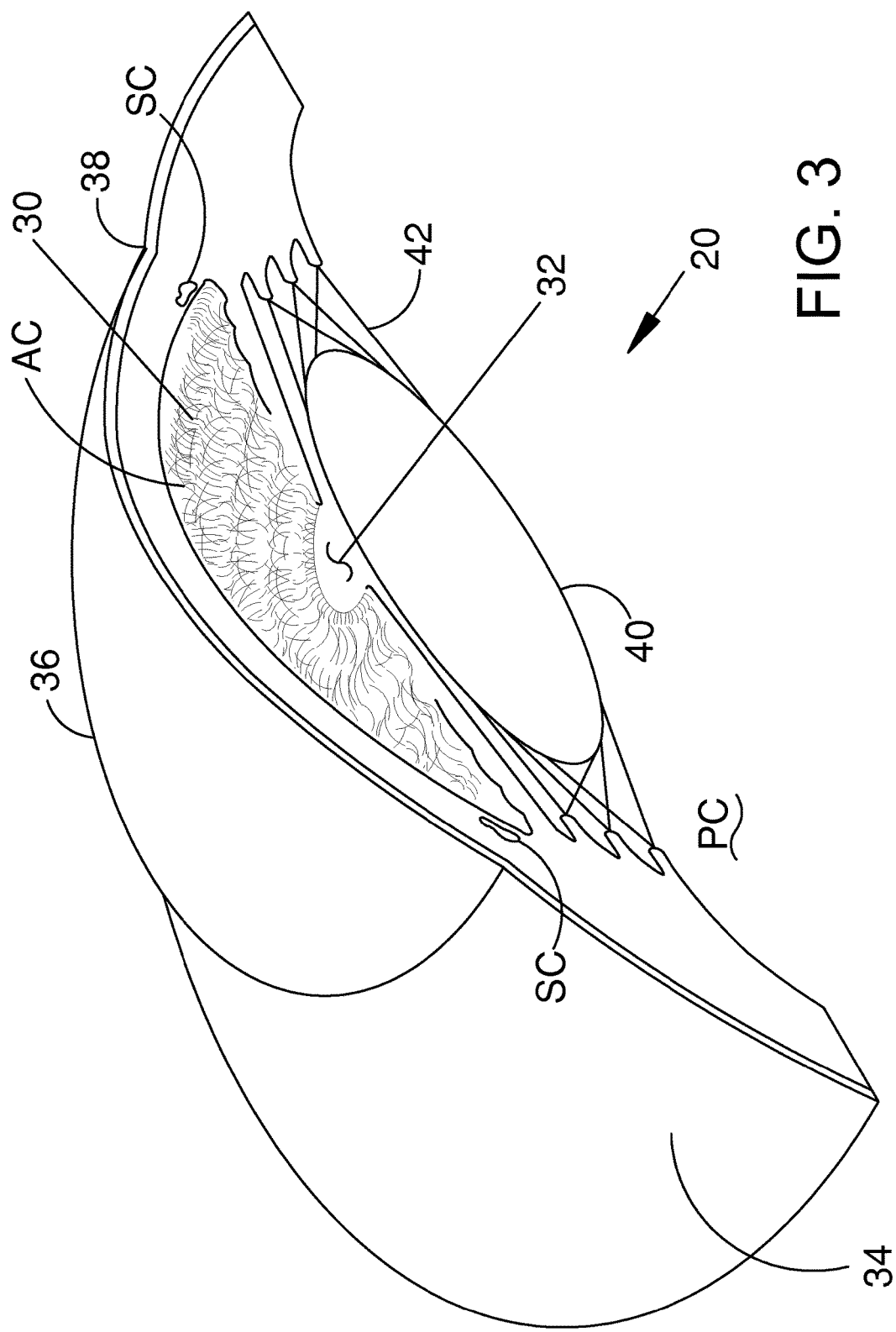
FIG. 3 is a stylized perspective view illustrating the anatomy of an eye.

FIG. 3 is a stylized perspective view illustrating a portion of eye 20 discussed above. Eye 20 includes an iris 30 defining a pupil 32. In FIG. 3, eye 20 is shown as a cross-sectional view created by a cutting plane passing through the center of pupil 32. Eye 20 can be conceptualized as a fluid filled ball having two chambers. Sclera 34 of eye 20 surrounds a posterior chamber PC filled with a viscous fluid known as vitreous humor. Cornea 36 of eye 20 encloses an anterior chamber AC that is filled with a fluid known as aqueous humor. The cornea 36 meets the sclera 34 at a limbus 38 of eye 20. A lens 40 of eye 20 is located between anterior chamber AC and posterior chamber PC. Lens 40 is held in place by a number of ciliary zonules 42.

Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

Schlemm's canal SC is a tube-like structure that encircles iris 30. Two laterally cut ends of Schlemm's canal SC are visible in the cross-sectional view of FIG. 3. In a healthy eye, aqueous humor flows out of anterior chamber AC and into Schlemm's canal SC. Aqueous humor exits Schlemm's canal SC and flows into a number of collector channels. After leaving Schlemm's canal SC, aqueous humor is absorbed into the venous blood stream and carried out of the eye.

Figure 4:
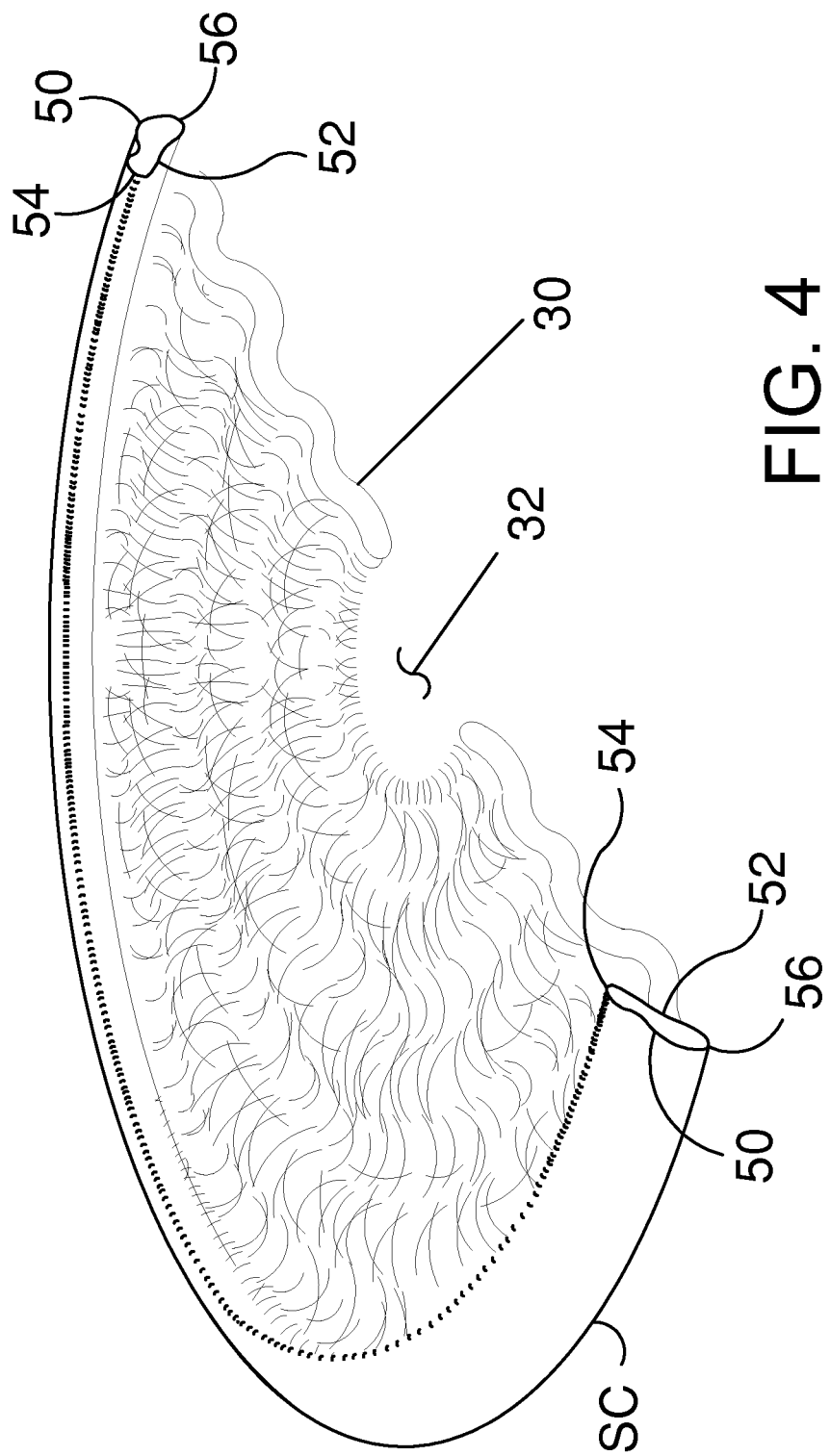
FIG. 4 is a stylized perspective view showing Schlemm's canal and an iris of the eye shown in the previous Figure.

FIG. 4 is a stylized perspective view showing Schlemm's canal SC and iris 30 of eye 20 shown in the previous Figure. In FIG. 4, Schlemm's canal SC is shown encircling iris 30. With reference to FIG. 4, it will be appreciated that Schlemm's canal SC may overhang iris 30 slightly. Iris 30 defines a pupil 32. In the embodiment of FIG. 4, Schlemm's canal SC and iris 30 are shown in cross-section, with a cutting plane passing through the center of pupil 32.

The shape of Schlemm's canal SC is somewhat irregular, and can vary from patient to patient. The shape of Schlemm's canal SC may be conceptualized as a cylindrical-tube that has been partially flattened. With reference to FIG. 4, it will be appreciated that Schlemm's canal SC has a first major side 50, a second major side 52, a first minor side 54, and a second minor side 56.

Schlemm's canal SC forms a ring around iris 30 with pupil 32 disposed in the center of that ring. With reference to FIG. 4, it will be appreciated that first major side 50 is on the outside of the ring formed by Schlemm's canal SC and second major side 52 is on the inside of the ring formed by Schlemm's canal SC. Accordingly, first major side 50 may be referred to as an outer major side of Schlemm's canal SC and second major side 52 may be referred to as an inner major side of Schlemm's canal SC. With reference to FIG. 4, it will be appreciated that first major side 50 is further from pupil 32 than second major side 52.

Figure 5:
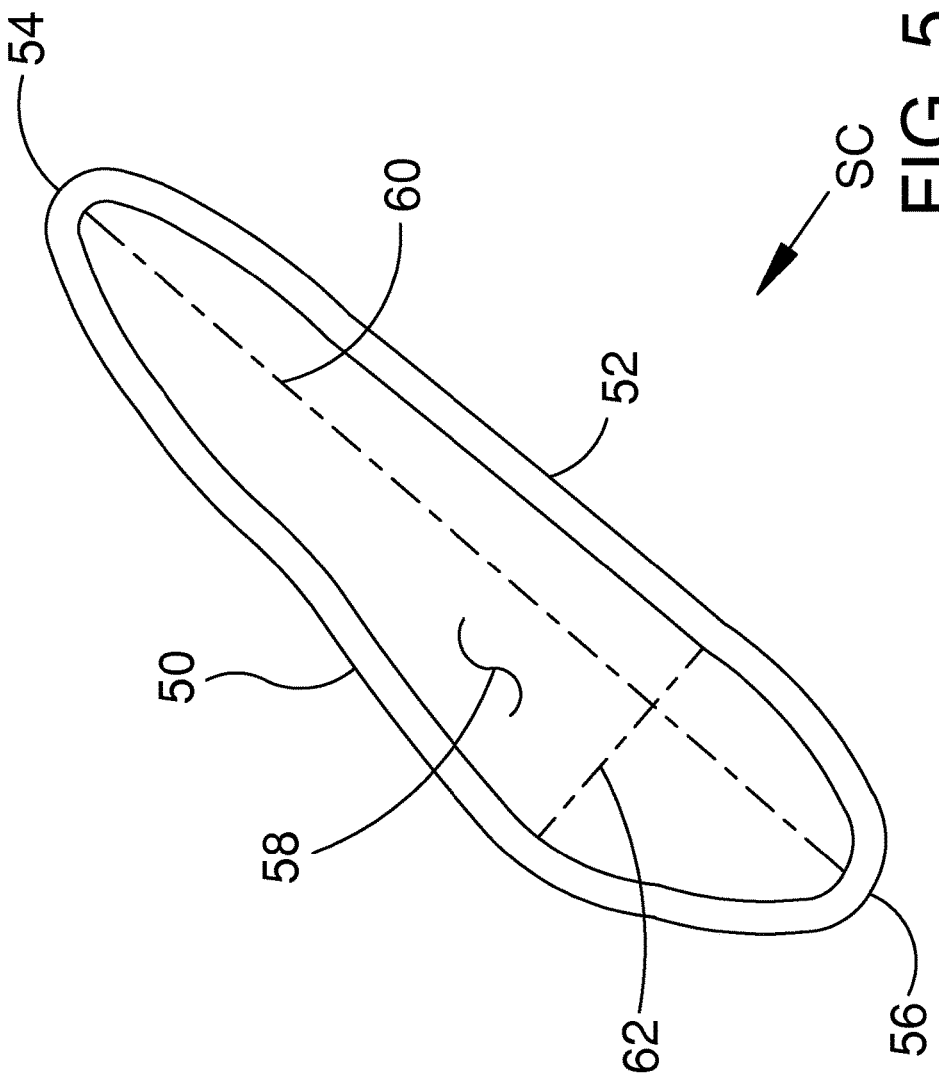
FIG. 5 is an enlarged cross-sectional view further illustrating Schlemm's canal SC shown in the previous Figure.

FIG. 5 is an enlarged cross-sectional view further illustrating Schlemm's canal SC shown in the previous Figure. With reference to FIG. 5, it will be appreciated that Schlemm's canal SC comprises a wall W defining a lumen 58. The shape of Schlemm's canal SC is somewhat irregular, and can vary from patient to patient. The shape of Schlemm's canal SC may be conceptualized as a cylindrical-tube that has been partially flattened. The cross-sectional shape of lumen 58 may be compared to the shape of an ellipse. A major axis 60 and a minor axis 62 of lumen 58 are illustrated with dashed lines in FIG. 5.

The length of major axis 60 and minor axis 62 can vary from patient to patient. The length of minor axis 62 is between one and thirty micrometers in most patients. The length of major axis 60 is between one hundred and fifty micrometers and three hundred and fifty micrometers in most patients.

With reference to FIG. 5, it will be appreciated that Schlemm's canal SC comprises a first major side 50, a second major side 52, a first minor side 54, and a second minor side 56. In the embodiment of FIG. 5, first major side 50 is longer than both first minor side 54 and second minor side 56. Also in the embodiment of FIG. 5, second major side 52 is longer than both first minor side 54 and second minor side 56.

Figure 6:
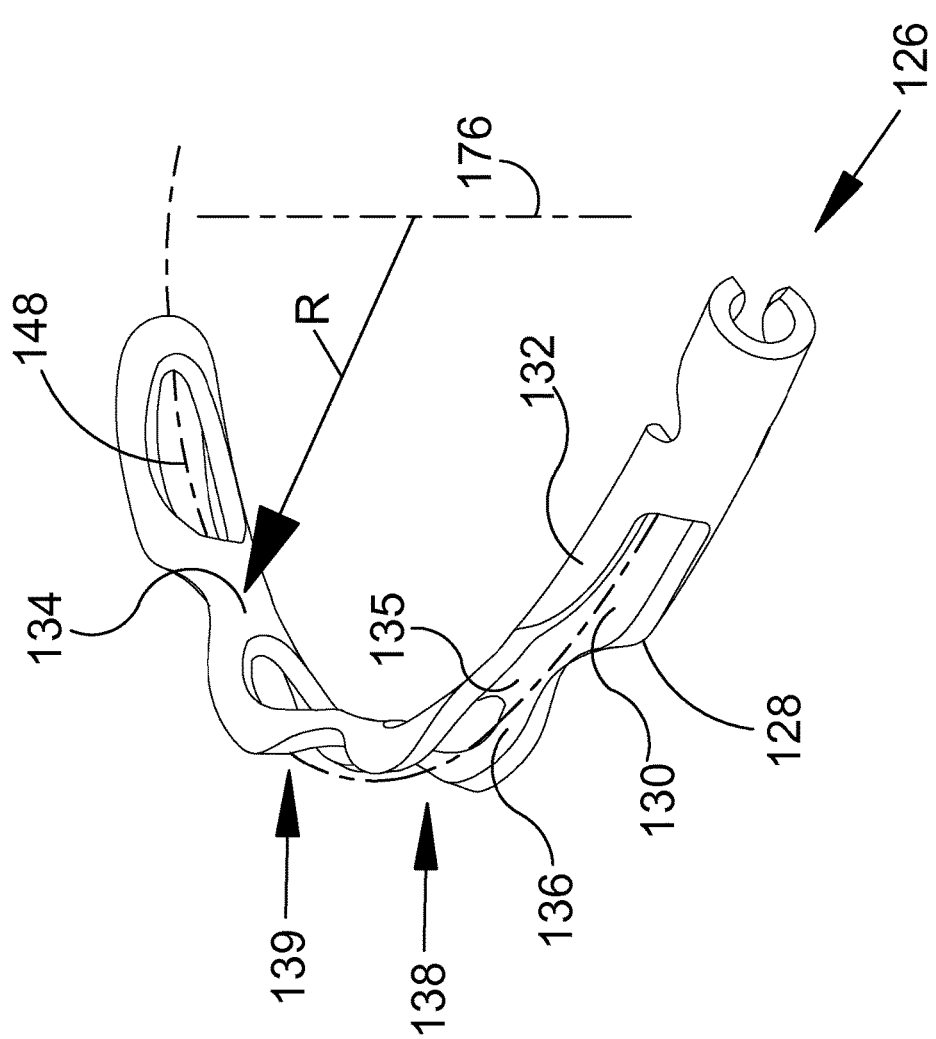
FIG. 6 is a perspective view showing an ocular implant in accordance with this detailed description.

FIG. 6 is a perspective view showing an ocular implant in accordance with this detailed description. Ocular implant 126 of FIG. 6 comprises a body 128 that extends along a generally curved longitudinal central axis 148. In the embodiment of FIG. 6, body 128 has a radius of curvature R that is represented with an arrow extending between a lateral central axis 176 and body 128.

Body 128 of ocular implant 126 has a first major surface 130 and a second major surface 132. With reference to FIG. 6, it will be appreciated that body 128 is curved about longitudinal central axis 148 so that first major surface 130 comprises a concave surface 136 and second major surface 132 comprises a convex surface 134. The curvature of body 128 can be pre-sized and configured to align with the curvature of Schlemm's canal in a patient's eye.

A distal portion of body 128 defines a longitudinal channel 138 including a channel opening 139. Channel opening 139 is disposed diametrically opposite a central portion 135 of concave surface 136. Because of the curvature of the body 128, an outer diameter of the implant defined by the channel opening 139 will be greater than an inner diameter of the implant defined by surface 132. In some embodiments, the body is pre-biased to assume a configuration in which the channel opening 139 is disposed along an outer diameter of the body, ensuring that the channel opening can be positioned adjacent to the first major side 50 of Schlemm's canal.

In the embodiment of FIG. 6, central portion 135 of concave surface 136 defines a plurality of apertures 137. Each aperture 137 fluidly communicates with channel 138. In some useful embodiments, body 128 is adapted and configured such that ocular implant 126 assumes an orientation in which channel opening 139 is adjacent a major side of Schlemm's canal when ocular implant 126 is disposed in Schlemm's canal. Ocular implant 126 can be made, for example, by laser cutting body 128 from a length of metal or a shape memory material (e.g., nitinol or stainless steel) tubing.

Figure 7A:
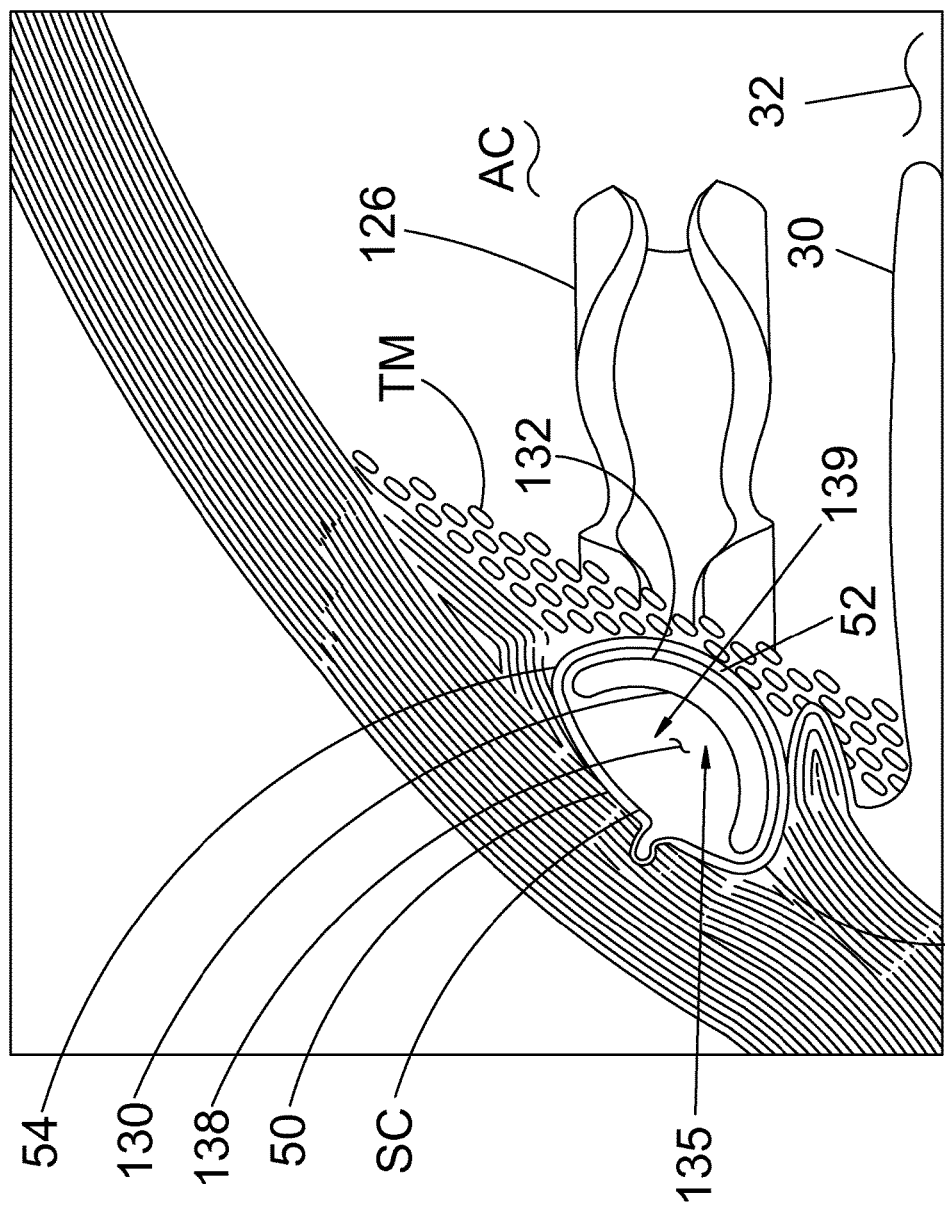
FIG. 7A and FIG. 7B are section views showing an ocular implant disposed in Schlemm's canal of an eye.
Figure 7B:
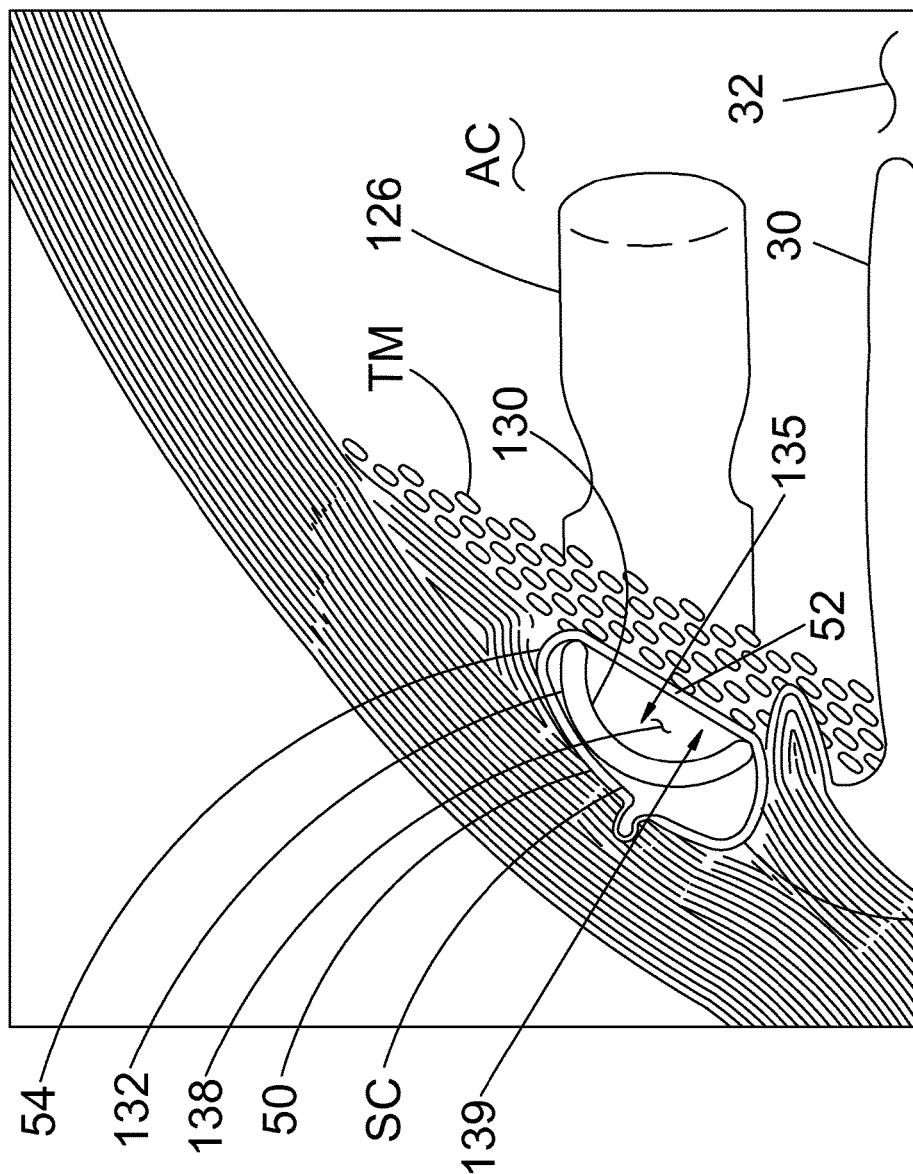

FIG. 7A and FIG. 7B are section views showing an ocular implant 126 disposed in Schlemm's canal SC of an eye. FIG. 7A and FIG. 7B may be collectively referred to as FIG. 7. The eye of FIG. 7 includes an iris 30. A central portion of iris 30 defines a pupil 32. Schlemm's canal SC is disposed near an outer edge of iris 30. The trabecular meshwork TM extends up from the iris of overlays Schlemm's canal SC. The picture plane of FIG. 7 extends laterally across Schlemm's canal SC and the trabecular meshwork TM.

Schlemm's canal SC forms a ring around iris 30 with pupil 32 disposed in the center of that ring. Schlemm's canal SC has a first major side 50, a second major side 52, a first minor side 54, and a second minor side 56. With reference to FIG. 7, it will be appreciated that first major side 50 is further from pupil 32 than second major side 52. In the embodiment of FIG. 7, first major side 50 is an outer major side of Schlemm's canal SC and second major side 52 is an inner major side of Schlemm's canal SC.

In the embodiment of FIG. 7A, a distal portion of ocular implant 126 is shown resting in Schlemm's canal SC. A proximal portion of ocular implant 126 is shown extending out of Schlemm's canal SC, through trebecular meshwork TM and into anterior chamber AC. Ocular implant 126 of FIG. 7 comprises a body having a first major surface 130 and a second major surface 132. With reference to FIG. 6, it will be appreciated that the body of ocular implant 126 is curved about a longitudinal central axis so that first major surface 130 comprises a concave surface and second major surface 132 comprises a convex surface.

A distal portion of ocular implant 126 defines a longitudinal channel 138 including a channel opening 139. Channel opening 139 is disposed diametrically opposite a central portion 135 of first major surface 130. In the embodiment of FIG. 7A, ocular implant 126 is assuming an orientation in which channel opening 139 is adjacent and open to first major side 50 of Schlemm's canal. In the embodiment of FIG. 7B, ocular implant 126 is assuming an orientation in which channel opening 139 is adjacent and open to second major side 52 of Schlemm's canal.

FIG. 8A, FIG. 8B and FIG. 8C illustrate multiple plan views of an implant 126 in accordance with the present detailed description. FIG. 8A, FIG. 8B and FIG. 8C may be referred to collectively as FIG. 8. It is customary to refer to multi-view projections using terms such as front view, top view, and side view. In accordance with this convention, FIG. 8A may be referred to as a top view of implant 126, FIG. 8B may be referred to as a side view of implant 126, and FIG. 8C may be referred to as a bottom view of implant 126. The terms top view, side view, and bottom view are used herein as a convenient method for differentiating between the views shown in FIG. 8. It will be appreciated that the implant shown in FIG. 8 may assume various orientations without deviating from the spirit and scope of this detailed description. Accordingly, the terms top view, side view, and bottom view should not be interpreted to limit the scope of the invention recited in the attached claims.

Ocular implant 126 of FIG. 8 comprises a body 128 that extends along a longitudinal central axis 148. Body 128 of ocular implant 126 has a first major surface 130 and a second major surface 132. In the embodiment of FIG. 8, body 128 is curved about longitudinal central axis 148 so that first major surface 130 comprises a concave surface 136 and second major surface 132 comprises a convex surface 134.

A distal portion of body 128 defines a longitudinal channel 138 including a channel opening 139. Channel opening 139 is disposed diametrically opposite a central portion 135 of concave surface 136. In the embodiment of FIG. 8, central portion 135 of concave surface 136 defines a plurality of apertures 137. Each aperture 137 fluidly communicates with channel 138. In some useful embodiments, body 128 is adapted and configured such that ocular implant 126 assumes an orientation in which channel opening 139 is adjacent a major side of Schlemm's canal when ocular implant 126 is disposed in Schlemm's canal.

Figure 9:
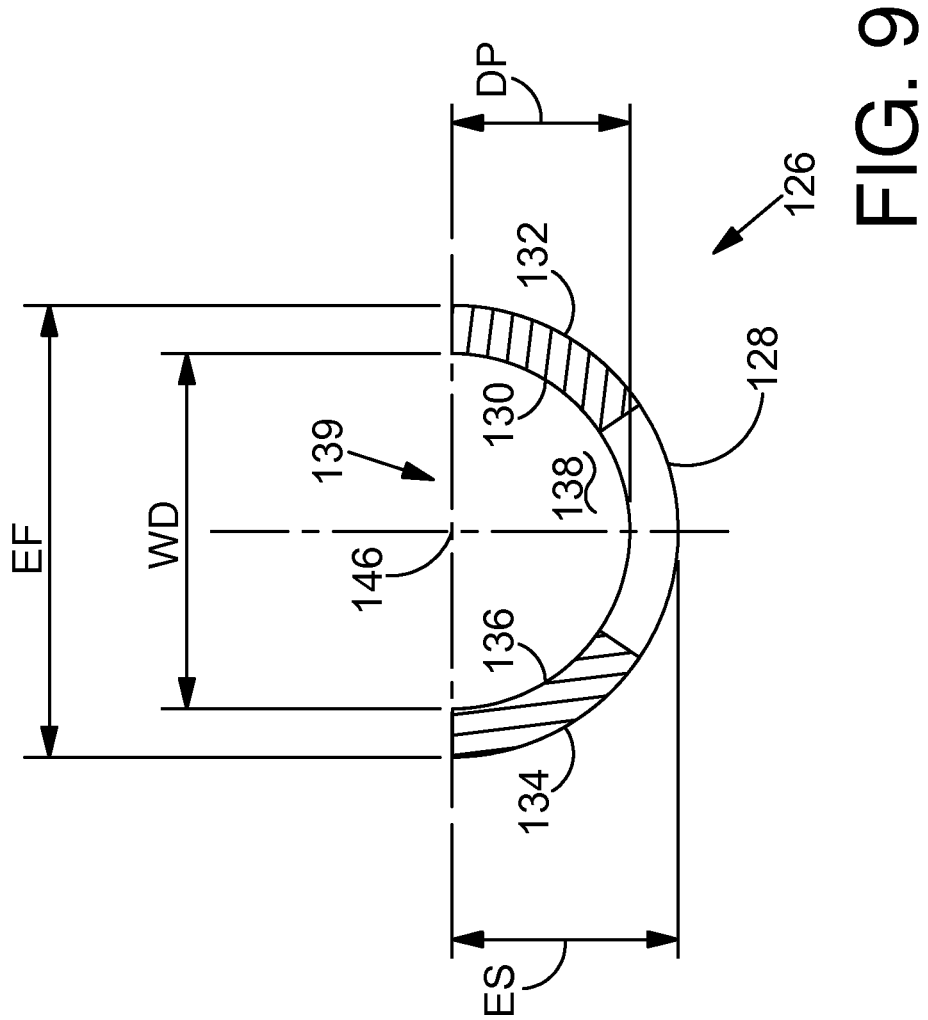
FIG. 9 is a lateral cross-sectional view of an ocular implant taken along section line A-A shown in the previous Figure.

FIG. 9 is a lateral cross-sectional view of ocular implant 126 taken along section line A-A shown in the previous Figure. Ocular implant 126 comprises a body 128 having a first major surface 130 and a second major surface 132. With reference to FIG. 9, it will be appreciated that body 128 curves around a longitudinal central axis 148 so that first major surface 130 comprises a concave surface 136 and second major surface 132 comprises a convex surface 134. The concave surface 136 of body 128 defines a longitudinal channel 138 having a channel opening 139.

As shown in FIG. 9, channel 138 has a width WD and a depth DP. Body 128 of ocular implant 126 has a first lateral extent EF and a second lateral extent ES. In some cases, body 128 is adapted and configured such that ocular implant 126 automatically assumes an orientation in which the channel opening is adjacent a major side of Schlemm's canal when ocular implant 126 is disposed in Schlemm's canal. In some useful embodiments, an aspect ratio of first lateral extent EF to second lateral extent ES is greater than about one. In some particularly useful embodiments, the aspect ratio of first lateral extent EF to second lateral extent ES is about two. In some useful embodiments, the aspect ratio of first lateral extent EF to second lateral extent ES is greater than about two. In some useful embodiments, an aspect ratio of channel width WD to channel depth DP is greater than about one. In some particularly useful embodiments, the aspect ratio of channel width WD to channel depth DP is about two. In some useful embodiments, the aspect ratio of channel width WD to channel depth DP is greater than about two.

Figure 10A:
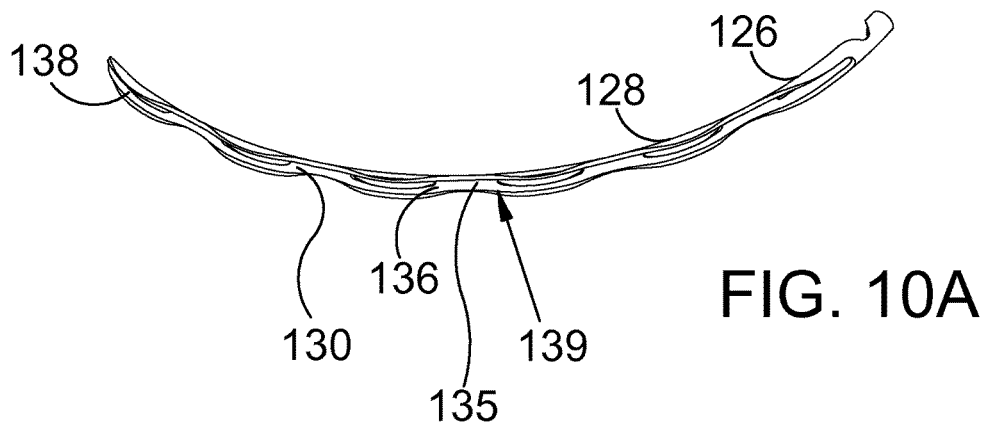
FIG. 10A is a perspective view of an ocular implant and FIG. 10B is a stylized perspective view showing Schlemm's canal SC encircling an iris.
Figure 10B:
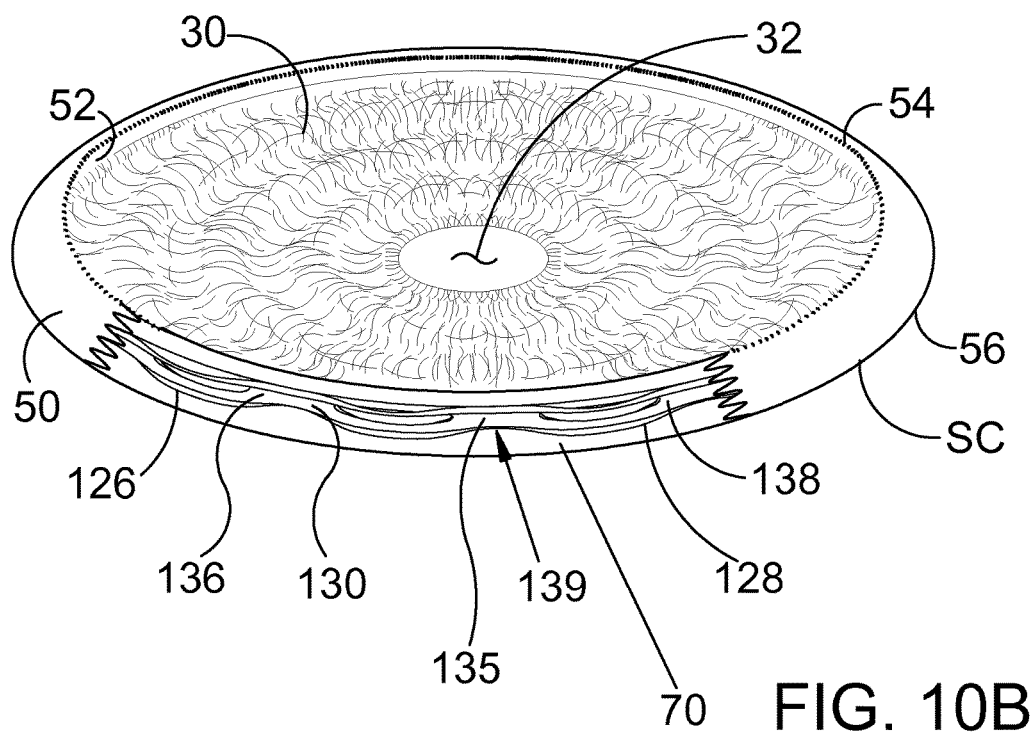

FIG. 10A is a perspective view of an ocular implant 126 and FIG. 10B is a stylized perspective view showing Schlemm's canal SC encircling an iris 30. FIG. 10A and FIG. 10B may be collectively referred to as FIG. 10. With reference to FIG. 10B, it will be appreciated that Schlemm's canal SC may overhang iris 30 slightly. Iris 30 defines a pupil 32. Schlemm's canal SC forms a ring around iris 30 with pupil 32 disposed in the center of that ring. With reference to FIG. 10B, it will be appreciated that Schlemm's canal SC has a first major side 50, a second major side 52, a first minor side 54, and a second minor side 56. With reference to FIG. 10B, it will be appreciated that first major side 50 is further from pupil 32 than second major side 52. In the embodiment of FIG. 10B, first major side 50 is an outer major side of Schlemm's canal SC and second major side 52 is an inner major side of Schlemm's canal SC.

For purposes of illustration, a window 70 is cut through first major side 50 of Schlemm's canal SC in FIG. 10B. Through window 70, an ocular implant 126 can be seen residing in a lumen defined by Schlemm's canal. Ocular implant 126 of FIG. 10 comprises a body 128 having a first major surface 130. First major surface 130 of body 128 comprises a concave surface 136. Body 128 defines a longitudinal channel 138 including a channel opening 139. Channel opening 139 is disposed diametrically opposite a central portion 135 of concave surface 136. In the embodiment of FIG. 10B, ocular implant 126 is assuming an orientation in which channel opening 139 is adjacent first major side 50 of Schlemm's canal.

Figure 11B:
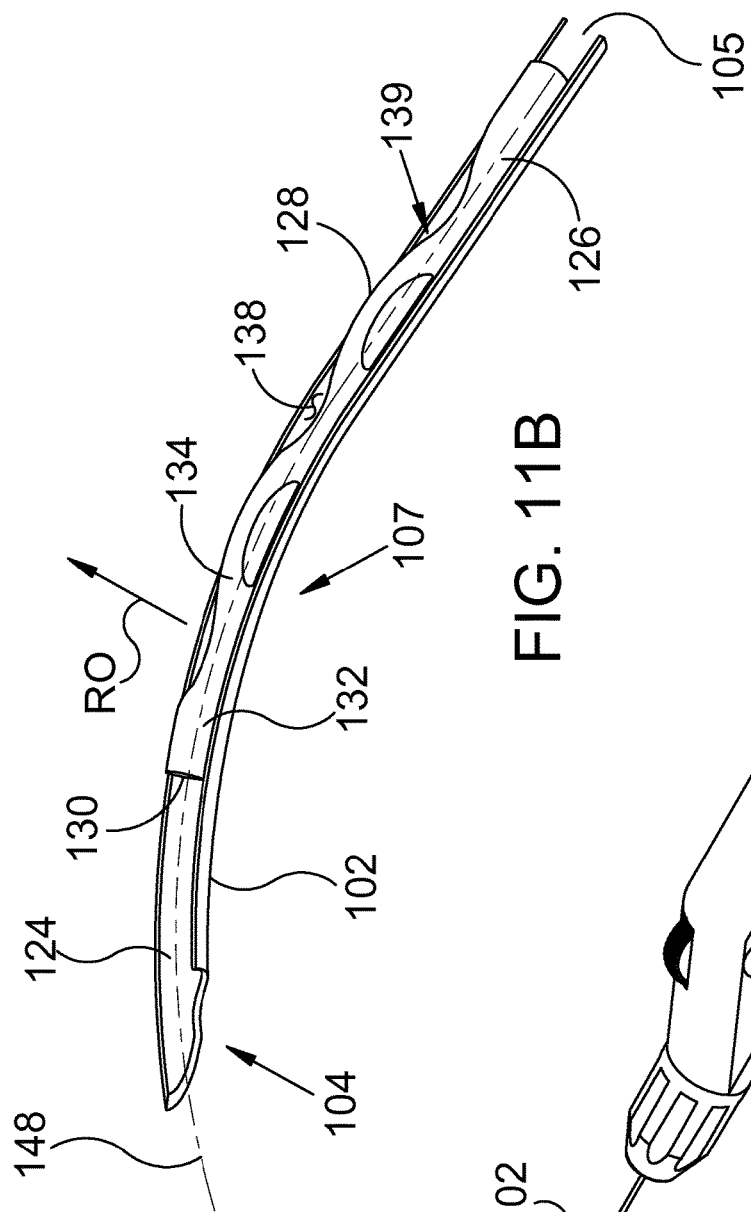
FIG. 11B is an enlarged detail view illustrating a cannula portion of the delivery system.
Figure 11A:
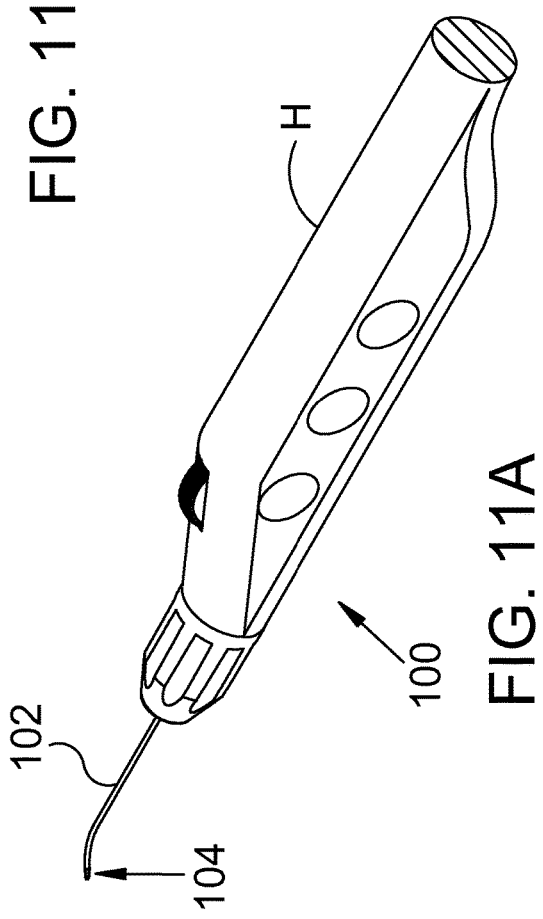
FIG. 11A is a perspective view showing a delivery system 100 that may be used to advance an ocular implant into Schlemm's canal of an eye.

FIG. 11A is a perspective view showing a delivery system 100 that may be used to advance an ocular implant 126 into Schlemm's canal of an eye. Delivery system 100 includes a cannula 102 that is coupled to a handle H. Cannula 102 defines a distal opening 104. The distal portion of cannula 102 of delivery system 100 is configured and adapted to be inserted into the anterior chamber of a human subject's eye so that distal opening 104 is positioned near Schlemm's canal of the eye. Cannula 102 is sized and configured so that the distal end of cannula 102 can be advanced through the trabecular meshwork of the eye and into Schlemm's canal. Positioning cannula 102 in this way places distal opening 104 in fluid communication with Schlemm's canal.

In the embodiment of FIG. 11A, an ocular implant is disposed in a passageway defined by cannula 102. Delivery system 100 includes a mechanism that is capable of advancing and retracting the ocular implant along the length of cannula 102. The ocular implant may be placed in Schlemm's canal of eye 20 by advancing the ocular implant through distal opening 104 of cannula 102 while distal opening 104 is in fluid communication with Schlemm's canal.

FIG. 11B is an enlarged detail view further illustrating cannula 102 of delivery system 100. With reference to FIG. 11B, it will be appreciated that cannula 102 comprises a tubular member defining a distal opening 104, a proximal opening 105, and a passageway 124 extending between proximal opening 105 and distal opening 104. With reference to FIG. 11B, it will be appreciated that cannula 102 includes a curved portion 107 disposed between distal opening 104 and proximal opening 105.

In the embodiment of FIG. 11B, an ocular implant 126 is disposed in passageway 124 defined by cannula 102. Ocular implant 126 of FIG. 11B comprises a body 128 that extends along a generally curved longitudinal central axis 148. Body 128 of ocular implant 126 has a first major surface 130 and a second major surface 132. With reference to FIG. 11B, it will be appreciated that body 128 is curved about longitudinal central axis 148 so that first major surface 130 defines a longitudinal channel 138 and second major surface 132 comprises a convex surface 134. Longitudinal channel 138 includes a channel opening 139. Ocular implant 126 is orient relative to delivery cannula 102 such that longitudinal channel 138 of ocular implant 126 opens in a radially outward direction RD when ocular implant 126 is disposed in curved portion 107. Radially outward direction RD is illustrated using an arrow in FIG. 11B. Distal opening 104 of cannula 102 may be placed in fluid communication with Schlemm's canal of an eye. Implant 126 may be advanced through distal opening 104 and into Schlemm's canal while assuming the orientation shown in FIG. 11B. When this is the case, ocular implant 126 may be oriented such that channel opening 139 is adjacent an outer major side of Schlemm's canal when ocular implant 126 is disposed in Schlemm's canal.

Figure 12:
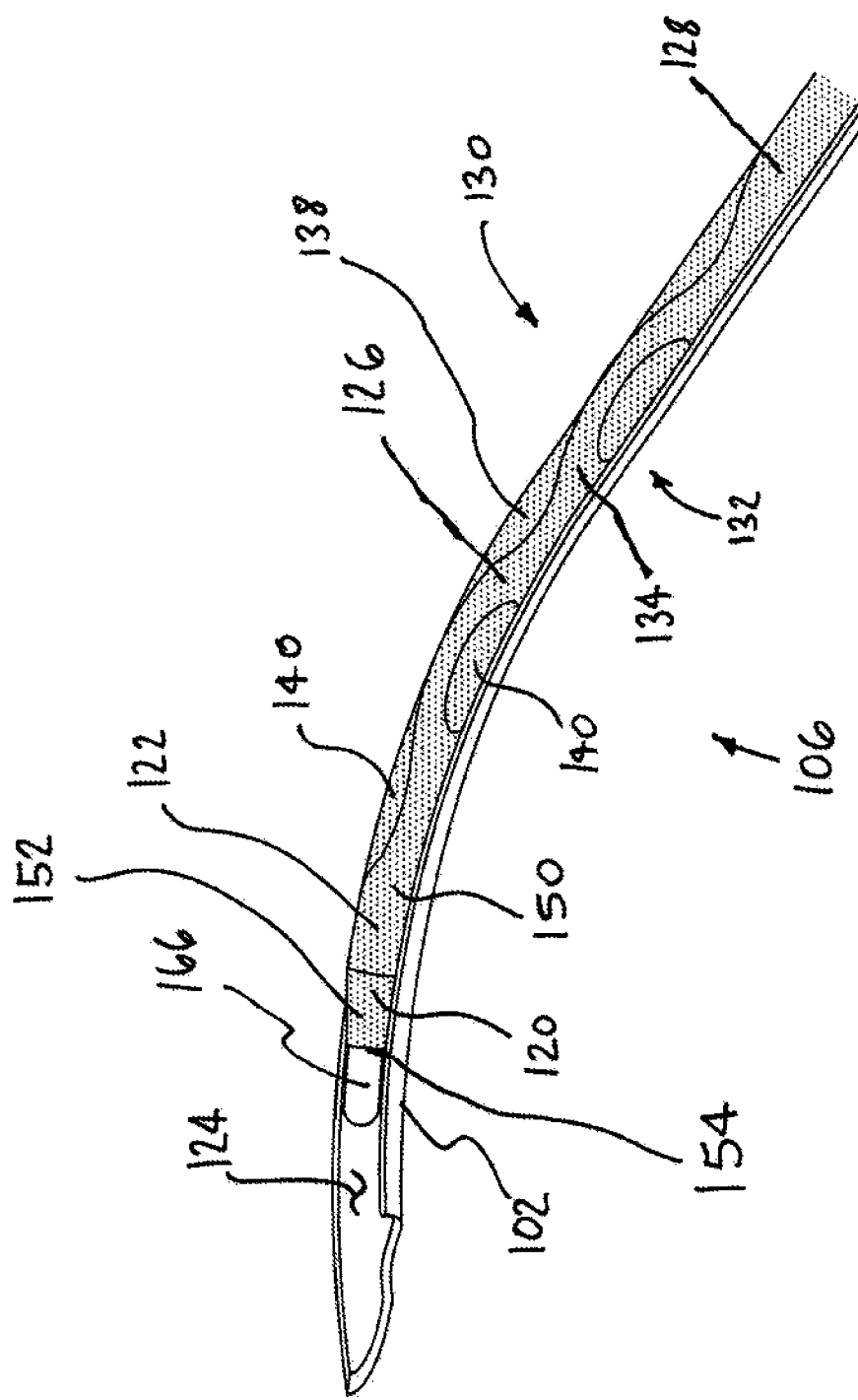
FIG. 12 is an enlarged perspective view of an assembly including a cannula, an ocular implant, and a sheath.

FIG. 12 is an enlarged perspective view of an assembly 106 including an ocular implant 126, a sheath 120, and a cannula 102. For purposes of illustration, cannula 102 is cross-sectionally illustrated in FIG. 12. In the embodiment of FIG. 12, a sheath 120 is shown extending into a passageway 124 defined by cannula 102. In FIG. 12, sheath 120 is illustrated in a transparent manner with a pattern of dots indicating the presence of sheath 120.

With reference to FIG. 12, it will be appreciated that an implant 126 is disposed in a lumen 122 defined by sheath 120. Implant 126 comprises a body 128 having a first major surface 130 and a second major surface 132. In the embodiment of FIG. 12, body 128 curves around a longitudinal central axis so that first major surface 130 comprises a concave surface and second major surface 132 comprises a convex surface 134. The concave surface of body 128 defines a longitudinal channel 138. In FIG. 12, a core 166 is shown extending through longitudinal channel 138.

Body 128 of ocular implant 126 defines a plurality of openings 140. In the embodiment of FIG. 12, sheath 120 is covering openings 140. With reference to FIG. 12, it will be appreciated that sheath 120 comprises a proximal portion 150 defining a lumen 122 and a distal portion 152 defining a distal aperture 154. Core 166 is shown extending through distal aperture 154 in FIG. 12. In the embodiment of FIG. 12, distal portion 152 of sheath 120 has a generally tapered shape.

Figure 13:
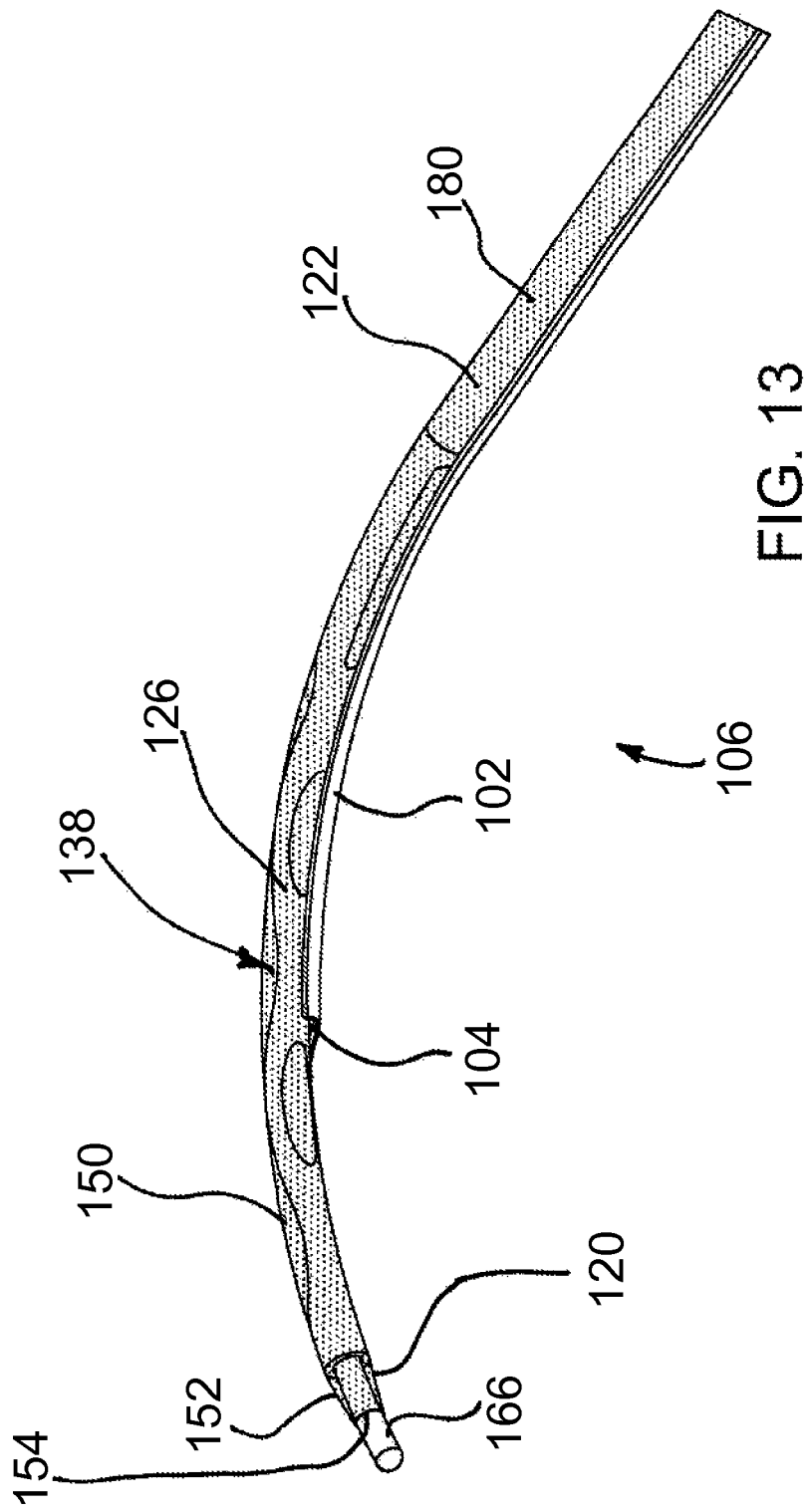
FIG. 13 is an additional perspective view of the assembly shown in the previous Figure.

FIG. 13 is an additional perspective view of assembly 106 shown in the previous Figure. In FIG. 13, core 166, sheath 120, and implant 126 are shown extending through a distal port 104 of cannula 102. Core 166, sheath 120, and implant 126 have been moved in a distal direction relative to the position of those elements shown in the previous Figure.

A push tube 180 is visible in FIG. 13. In FIG. 13, a distal end of push tube 180 is shown contacting a proximal end of implant 126. In the embodiment of FIG. 13, push tube 180 is disposed in a lumen 122 defined by sheath 120. Sheath 120 comprises a proximal portion 150 defining a passageway 124 and a distal portion 152 defining a distal aperture 154. Implant 126 is disposed in lumen 122 defined by sheath 120. In FIG. 13, core 166 is shown extending through a channel 138 defined by implant 126 and a distal aperture 154 defined by distal portion 152 of sheath 120.

Figure 14:
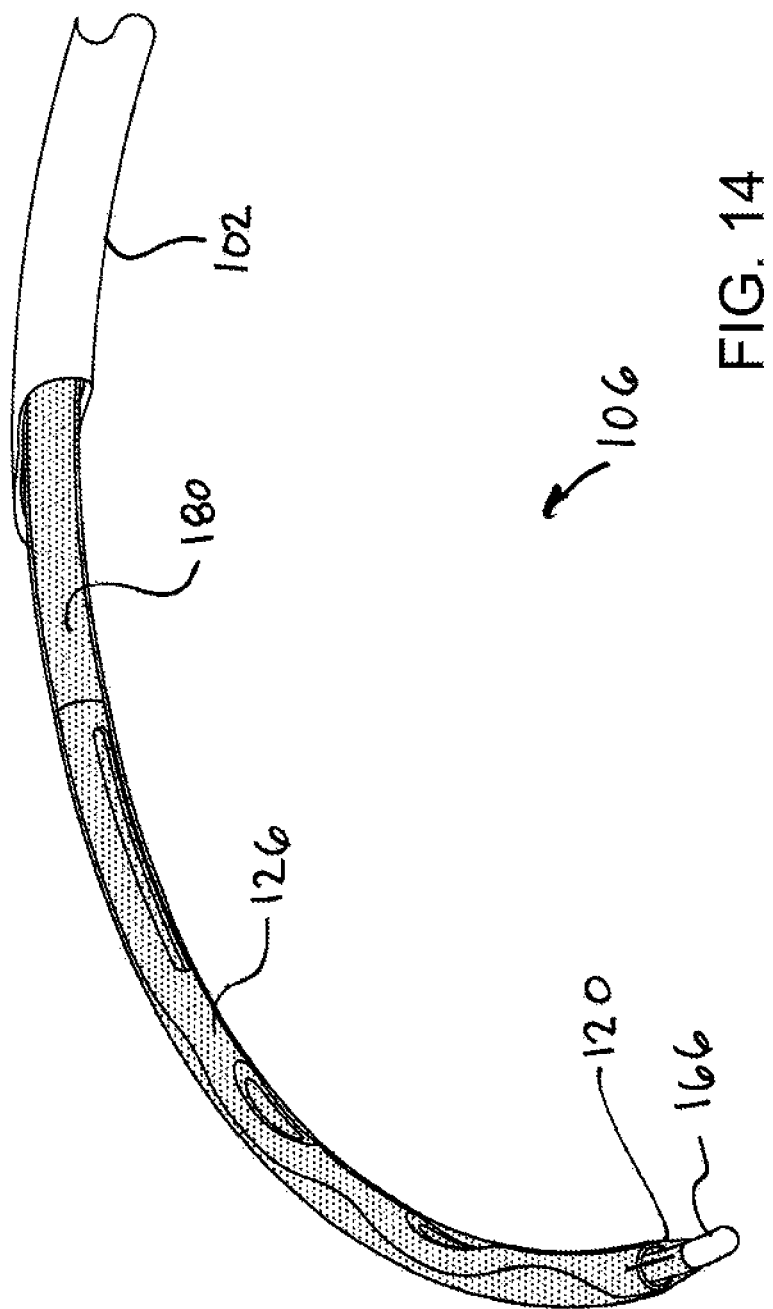
FIG. 14 is another perspective view of an assembly including a cannula, an ocular implant, and a sheath.

FIG. 14 is an additional perspective view showing assembly 106 shown in the previous Figure. With reference to FIG. 14, it will be appreciated that implant 126 is disposed outside of cannula 102. In the embodiment of FIG. 14, core 166, sheath 120, and push tube 180 have been advanced further so that implant 126 is in a position outside of cannula 102.

Methods in accordance with the present invention can be used to deliver an implant into Schlemm's canal of an eye. In these methods, a distal portion of core 166 and sheath 120 may be advanced out of the distal port of cannula 102 and into Schlemm's canal. Ocular implant 126 may be disposed inside sheath 120 while the distal portion of the sheath 120 is advanced into Schlemm's canal. Sheath 120 and core 166 may then be retracted while push tube 180 prevents implant 126 from being pulled proximally.

Figure 15:
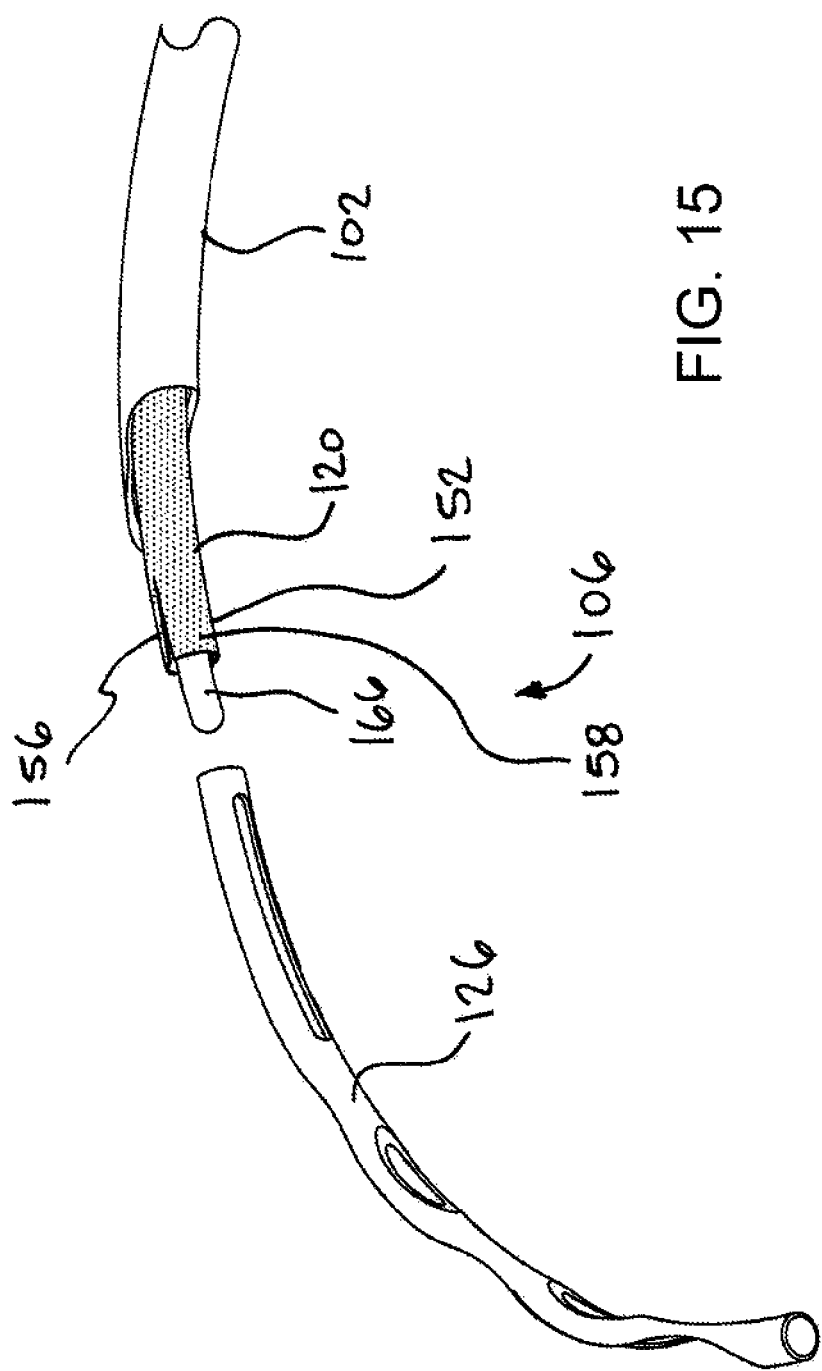
FIG. 15 is an additional perspective view of the assembly shown in the previous Figure.

FIG. 15 is an additional perspective view showing the assembly 106 shown in the previous Figure. In the embodiment of FIG. 15, core 166 and sheath 120 have been moved in a proximal direction relative to implant 126. With reference to FIG. 15, it will be appreciated that implant 126 is now disposed outside of sheath 120. Some methods in accordance with the present detailed description include the step of applying a proximally directed force to sheath 120 and core 166 while providing a distally directed reactionary force on implant 126 to prevent implant 126 from moving proximally. When this is the case, implant 126 may pass through distal aperture 154 of sheath 120 as sheath 120 is retracted over implant 126.

In the embodiment of FIG. 15, distal portion 152 of sheath 120 comprises a first region 156 and a second region 158. The frangible connection between first region 156 and second region 158 has been broken in the embodiment of FIG. 15. This frangible connection may be selectively broken, for example, when sheath 120 is moved in a proximal direction relative to implant 126 due to the larger diameter of implant 126 with respect to the diameters of distal portion 152 and opening 154 of sheath 120. With reference to FIG. 15, it will be appreciated that the width of distal aperture 154 becomes larger when the frangible connection is broken.

With reference to the Figures described above, it will be appreciated that methods in accordance with the present detailed description may be used to position a distal portion of an implant in Schlemm's canal of an eye. A method in accordance with the present detailed description may include the step of advancing a distal end of a cannula through a cornea of the eye so that a distal portion of the cannula is disposed in the anterior chamber of the eye. The cannula may be used to access Schlemm's canal, for example, by piercing the wall of Schlemm's canal with a distal portion of the cannula. A distal portion of a sheath may be advanced out of a distal port of the cannula and into Schlemm's canal. An ocular implant may be disposed inside the sheath while the distal portion of the sheath is advanced into Schlemm's canal.

In some useful methods, the ocular implant comprises a body defining a plurality of apertures and the method includes the step of covering the apertures with a sheath. When this is the case, the distal portion of the implant may be advanced into Schlemm's canal while the apertures are covered by the sheath. Covering the apertures as the implant is advanced into Schlemm's canal may reduce the trauma inflicted on Schlemm's canal by the procedure. The apertures may be uncovered, for example, after the implant has reached a desired location (e.g., inside Schlemm's canal).

The apertures of the implant may be uncovered, for example, by moving the sheath in a proximal direction relative to the implant. In some applications, this may be accomplished by applying a proximal directed force to the sheath while holding the implant stationary. The implant may be held stationary, for example, by applying a distally directed reaction force on the implant. In one embodiment, a distally directed reaction force is provided by pushing on a proximal end of the implant with a push tube.

Some methods include the step of ceasing advancement of the sheath into Schlemm's canal when a proximal portion of the implant remains in an anterior chamber of the eye and a distal portion of the implant lies in Schlemm's canal. When this is the case, only a distal portion of the implant is advanced into Schlemm's canal. The portion of the implant extending out of Schlemm's canal and into the anterior chamber may provide a path for fluid flow between the anterior chamber and Schlemm's canal.

An assembly may be created by placing a core in a channel defined by the ocular implant. A sheath may be placed around the implant and the core. For example, the core and the implant may then be inserted into the lumen of a sheath. By way of another example, the sheath may be slipped over the implant and the core. The core may be withdrawn from the channel defined by the ocular implant, for example, after the implant has been delivered to a desired location.

The core may be withdrawn from the channel, for example, by moving the core in a proximal direction relative to the implant. In some applications, this may be accomplished by applying a proximal directed force to the core while holding the implant stationary. The implant may be held stationary, for example, by applying a distally directed reaction force on the implant. In one embodiment, a distally directed reaction force is provided by pushing on a proximal end of the implant with a push tube.

The core, the implant, and the sheath may be advanced into Schlemm's canal together. Once the implant is in a desired location, the core and the sheath may be withdrawn from the Schlemm's canal leaving the implant in the desired location. In some methods, the core and the sheath are withdrawn from Schlemm's canal simultaneously.

Figure 16B:
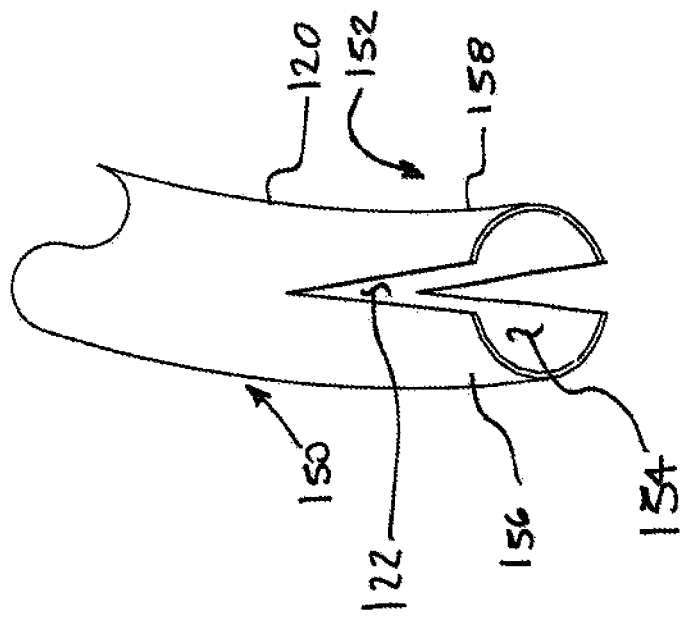
FIG. 16A and FIG. 16B are perspective views showing a sheath in accordance with the present detailed description.
Figure 16A:
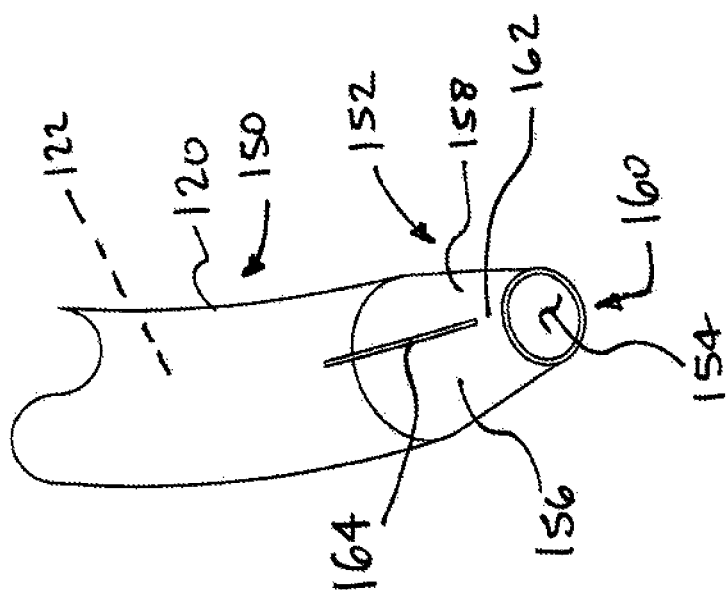

FIG. 16A and FIG. 16B are perspective views showing a sheath 120 in accordance with the present detailed description. FIG. 16A and FIG. 16B may be referred to collectively as FIG. 16. Sheath 120 of FIG. 16 comprises a proximal portion 150 defining a lumen 122 and a distal portion 152 defining a distal aperture 154. With reference to FIG. 16, it will be appreciated that lumen 122 is generally larger than distal aperture 154.

In the embodiment of FIG. 16A, distal portion 152 of sheath 120 comprises a first region 156, a second region 158, and a frangible connection 160 between first region 156 and second region 158. In FIG. 16A, a slit 164 defined by distal portion 152 is shown disposed between first region 156 and second region 158. In the embodiment of FIG. 16A, frangible connection 160 comprises a bridge 162 extending across slit 164.

In the embodiment of FIG. 16B, frangible connection 160 has been broken. Frangible connection 160 may be selectively broken, for example, by moving sheath 120 in a proximal direction relative to an implant disposed in lumen 122 having a diameter larger than the diameters of distal opening 154 and distal portion 152 of sheath 120. With reference to FIG. 16, it will be appreciated that distal aperture 154 becomes larger when frangible connection 160 is broken.

In the embodiment of FIG. 16, the presence of slit 164 creates a localized line of weakness in distal portion 152 of sheath 120. This localized line of weakness causes distal portion 152 to selectively tear in the manner shown in FIG. 16. It is to be appreciated that distal portion 152 may comprise various elements that create a localized line of weakness without deviating from the spirit and scope of the present detailed description. Examples of possible elements include: a skive cut extending partially through the wall of distal portion 120, a series of holes extending through the wall of distal portion 120, a perf cut, a crease, and a score cut.

Figure 17:
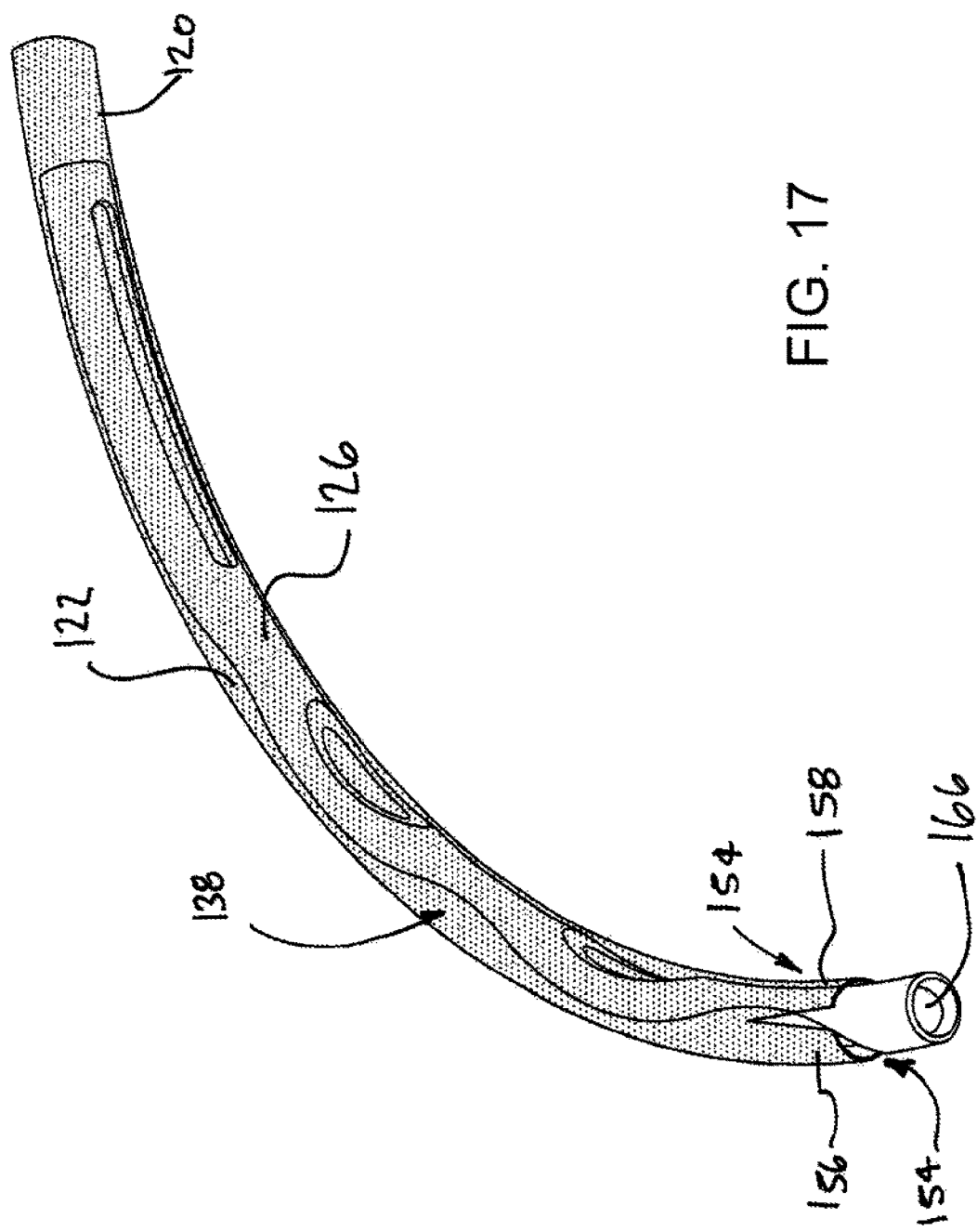
FIG. 17 is a perspective view of an assembly including the sheath shown in the previous Figure.

FIG. 17 is a perspective view of an assembly including sheath 120 shown in the previous Figure. In the embodiment of FIG. 17, an implant 126 is shown extending through distal aperture 154 defined by distal portion 152 of sheath 120. Implant 126 defines a channel 138. In FIG. 17, a core 166 can be seen resting in channel 138. Implant 126 and core 166 extend proximally into lumen 122 defined by sheath 120. Distal portion 152 of sheath 120 comprises a first region 156 and a second region 158.

FIG. 18A and FIG. 18B are simplified plan views showing a sheath 120 in accordance with the present detailed description. Sheath 120 comprises a distal portion 152 including a first region 156, a second region 158 and a frangible connection between first region 156 and second region 158. In the embodiment of FIG. 18A, frangible connection 160 is intact. In the embodiment of FIG. 18B, frangible connection 160 is broken. FIG. 18A and FIG. 18B may be referred to collectively as FIG. 18.

Sheath 120 of FIG. 18 comprises a proximal portion 150 defining a lumen 122. In the embodiment of FIG. 18, an implant 126 is disposed in lumen 122. Lumen 122 fluidly communicates with a distal aperture 154 defined by distal portion 152 of sheath 120. Distal portion 152 includes a slit 164 disposed between first region 156 and second region 158. In FIG. 18A, a bridge 162 can be seen spanning slit 164. In some useful embodiments, distal portion 152 of sheath 120 has a first hoop strength and proximal portion 150 sheath 120 has a second hoop strength. The first hoop strength may be limited by the frangible connection in the embodiment of FIG. 18A. When this is the case, the second hoop strength is greater than the first hoop strength.

Sheath 120 of FIG. 18 comprises a proximal portion 150 defining a lumen 122 and a distal portion 152 defining a distal aperture 154. Lumen 122 has a lumen width LW. Distal aperture has an aperture width AW when frangible connection 160 is intact. With reference to FIG. 18B, it will be appreciated that the distal aperture 154 is free to open further when frangible connection 160 is broken.

In some useful embodiments, lumen width LW of lumen 122 is equal to or greater than the width of an implant 126 disposed in lumen 122. In some of these useful embodiments, aperture width AW is smaller than the width of the implant 126. When this is the case, frangible connection 160 can be selectively broken by moving sheath 120 in a proximal direction relative to the implant 126.

FIG. 19A, FIG. 19B and FIG. 19C are multiple plan views of an implant 326 in accordance with the present detailed description. FIG. 19A, FIG. 19B and FIG. 19C may be referred to collectively as FIG. 19. FIG. 19A may be referred to as a top view of implant 326, FIG. 19B may be referred to as a side view of implant 326, and FIG. 19C may be referred to as a bottom view of implant 326. The terms top view, side view, and bottom view are used herein as a convenient method for differentiating between the views shown in FIG. 19. It will be appreciated that the implant shown in FIG. 19 may assume various orientations without deviating from the spirit and scope of this detailed description. Accordingly, the terms top view, side view, and bottom view should not be interpreted to limit the scope of the invention recited in the attached claims.

Ocular implant 326 of FIG. 19 comprises a body 328 that extends along a longitudinal central axis 348. Body 328 of ocular implant 326 has a first major surface 330 and a second major surface 332. In the embodiment of FIG. 19, body 328 is curved about longitudinal central axis 348 so that first major surface 330 comprises a concave surface 336 and second major surface 332 comprises a convex surface 334.

A distal portion of body 328 defines a longitudinal channel 338 including a channel opening 339. Channel opening 339 is disposed diametrically opposite a central portion 335 of concave surface 336. In the embodiment of FIG. 19, central portion 335 of concave surface 336 defines a plurality of apertures 337. Each aperture 337 fluidly communicates with channel 338.

Figure 20:
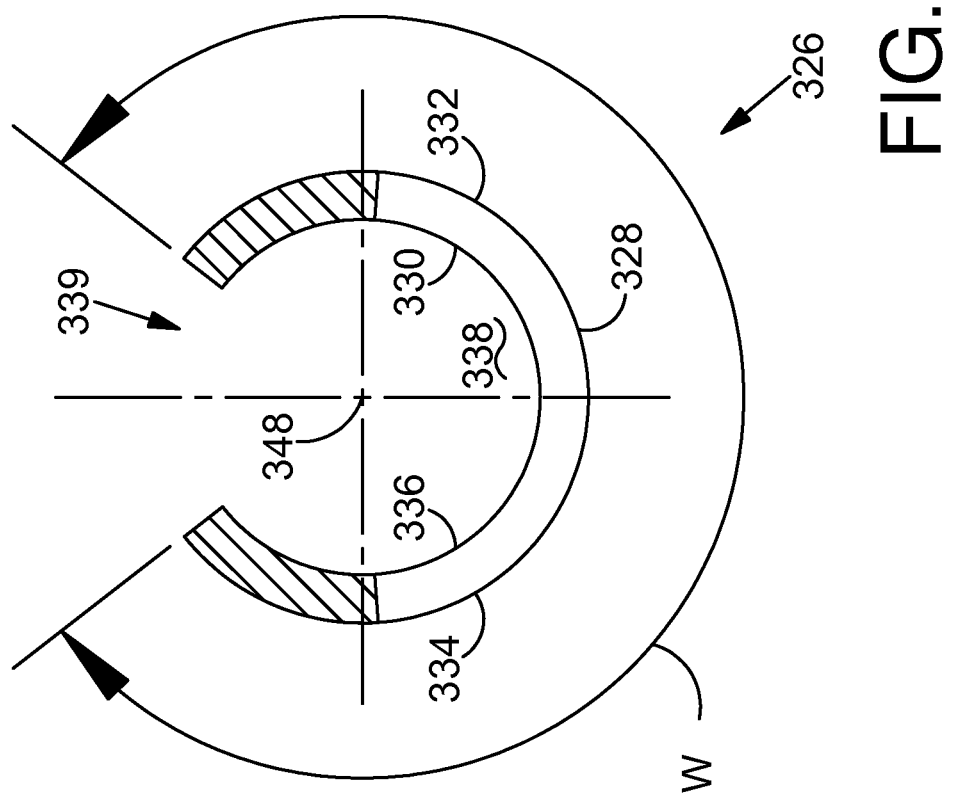
FIG. 20 is a lateral cross-sectional view of an ocular implant taken along section line A-A shown in the previous figure.

FIG. 20 is a lateral cross-sectional view of ocular implant 326 taken along section line B-B shown in the previous Figure. Ocular implant 326 comprises a body 328 having a first major surface 330 and a second major surface 332. With reference to FIG. 20, it will be appreciated that body 328 curves around a longitudinal central axis 348 so that first major surface 330 comprises a concave surface 336 and second major surface 332 comprises a convex surface 334. The concave surface 336 of body 328 defines a longitudinal channel 338 having a channel opening 339. As shown in FIG. 20, body 328 has a circumferential extent that spans an angle W. In the embodiment of FIG. 20, angle W has a magnitude that is greater than one hundred eighty degrees.

FIG. 21 is a cross-sectional view showing an implant 326 in accordance with the present detailed description. Ocular implant 326 of FIG. 21 comprises a body 328 that extends along a generally curved longitudinal central axis 348. In the embodiment of FIG. 21, body 328 has a distal radius of curvature RD and a proximal radius of curvature RP. Each radius of curvature is represented with an arrow in FIG. 21. Distal radius of curvature RD is represented by an arrow extending between a first lateral central axis 376 and a distal portion of longitudinal central axis 348. Proximal radius of curvature RP is represented by an arrow extending between a second lateral central axis 378 and a proximal portion of longitudinal central axis 348. In the embodiment of FIG. 21, body 328 of ocular implant 326 has an at rest shape that is generally curved. This at rest shape can be established, for example, using a heat-setting process. The rest shape of the implant can be generally aligned with the radius of curvature of Schlemm's canal in a human eye.

FIG. 22A, FIG. 22B and FIG. 22C are multiple plan views of an implant 526 in accordance with the present detailed description. FIG. 22A, FIG. 22B and FIG. 22C may be referred to collectively as FIG. 22. FIG. 22A may be referred to as a top view of implant 526, FIG. 22B may be referred to as a side view of implant 526, and FIG. 22C may be referred to as a bottom view of implant 526. The terms top view, side view, and bottom view are used herein as a convenient method for differentiating between the views shown in FIG. 22. It will be appreciated that the implant shown in FIG. 22 may assume various orientations without deviating from the spirit and scope of this detailed description. Accordingly, the terms top view, side view, and bottom view should not be interpreted to limit the scope of the invention recited in the attached claims.

Ocular implant 526 of FIG. 22 comprises a body 528 that extends along a longitudinal central axis 548. Body 528 of ocular implant 526 has a first major surface 530 and a second major surface 532. In the embodiment of FIG. 22, body 528 is curved about longitudinal central axis 548 so that first major surface 530 comprises a concave surface 536 and second major surface 532 comprises a convex surface 534.

A distal portion of body 528 defines a longitudinal channel 538 including a channel opening 539. Channel opening 539 is disposed diametrically opposite a central portion 535 of concave surface 536. In the embodiment of FIG. 22, central portion 535 of concave surface 536 defines a plurality of apertures 537. Each aperture 537 fluidly communicates with channel 538.

FIG. 23 is a lateral cross-sectional view of ocular implant 526 taken along section line C-C shown in the previous Figure. Ocular implant 526 comprises a body having a first major side 530 and a second major side 532. With reference to FIG. 23, it will be appreciated that body 528 curves around a longitudinal central axis 548 so that first major side 530 comprises a concave surface 536 and second major side 532 comprises a convex surface 534. The concave surface 536 of body 528 defines a longitudinal channel 538 having a channel opening 539. As shown in FIG. 23, body 528 has a circumferential extent that spans an angle C. In the embodiment of FIG. 23, angle C has a magnitude that is about one hundred eighty degrees. Some useful implants in accordance with the present detailed description comprise a body having a circumferential extend that spans an angle that is about one hundred eighty degrees. Some particularly useful implants in accordance with the present detailed description comprise a body having a circumferential extend that spans an angle that is equal to or less than one hundred eighty degrees.

FIG. 24 is a plan view showing an implant 526 in accordance with the present detailed description. Ocular implant 526 of FIG. 24 comprises a body 528 that extends along a generally curved longitudinal central axis 548. In the embodiment of FIG. 24, body 528 has a distal radius of curvature RD and a proximal radius of curvature RP. Each radius of curvature is represented with an arrow in FIG. 24. Distal radius of curvature RD is represented by an arrow extending between a first lateral central axis 576 and a distal portion of longitudinal central axis 548. Proximal radius of curvature RP is represented by an arrow extending between a second lateral central axis 578 and a proximal portion of longitudinal central axis 548. In the embodiment of FIG. 24, body 528 of ocular implant 526 has an at rest shape that is generally curved. This at rest shape can be established, for example, using a heat-setting process.

FIG. 25A through FIG. 25D are a series of plan views illustrating a method in accordance with the present detailed description. FIG. 25A is a plan view showing an implant 426. Implant 426 comprises a body 428 defining a plurality of openings 440. Openings 440 include a first opening 442 and a second opening 444.

FIG. 25B is a plan view showing an assembly 408 including implant 426. Assembly 408 of FIG. 25B may be created by placing a core 406 in a channel 438 defined by implant 426. A sheath 420 may be placed around implant 426 and core 406. For example, core 406 and implant 426 may be inserted into a lumen defined by sheath 420. By way of another example, sheath 420 may be slipped over implant 426 and core 406.

FIG. 25C is a plan view showing assembly 408 disposed in Schlemm's canal SC. The wall W of Schlemm's canal SC comprises a plurality of cells 90. With reference to FIG. 25C, it will be appreciated that sheath 420 is disposed between implant 426 and cells 90. A method in accordance with the present detailed description may include the step of advancing a distal end of a cannula through a cornea of the eye so that a distal portion of the cannula is disposed in the anterior chamber of the eye. The cannula may be used to access Schlemm's canal, for example, by piercing the wall of Schlemm's canal with a distal portion of the cannula. A distal portion of sheath 420 may be advanced out of a distal port of the cannula and into Schlemm's canal SC. Ocular implant 426 may be disposed inside sheath 420 while the distal portion of sheath 420 is advance into Schlemm's canal SC.

In the embodiment of FIG. 25C, ocular implant 426 comprises a body defining a plurality of openings 440. With reference to FIG. 25C, it will be appreciated that openings 440 are covered by sheath 420 and that a distal portion of implant 426 may be advanced into Schlemm's canal while openings 440 are covered by sheath 420. Covering openings 440 as implant 426 is advanced into Schlemm's canal SC may reduce the trauma inflicted on cells 90 by the procedure.

In some useful embodiments, sheath 420 comprises a coating disposed on an outer surface thereof. The properties of the coating may be selected to further reduce the trauma inflicted on cells 90 by the procedure. The coating may comprise, for example, a hydrophilic material. The coating may also comprise, for example, a lubricious polymer. Examples of hydrophilic materials that may be suitable in some applications include: polyalkylene glycols, alkoxy polyalkylene glycols, copolymers of methylvinyl ether and maleic acid poly(vinylpyrrolidone), poly(N-alkylacrylamide), poly(acrylic acid), poly(vinyl alcohol), poly(ethyleneimine), methyl cellulose, carboxymethyl cellulose, polyvinyl sulfonic acid, heparin, dextran, modified dextran and chondroitin sulphate.

In FIG. 25C, the distal portion of sheath 420 is shown extending between a smaller, distal diameter and a larger, proximal diameter. In the embodiment of FIG. 25C, the distal portion of sheath 420 has a generally tapered shape. The tapered transition of the distal portion of sheath 420 may create a non traumatic transition that dilates Schlemm's canal SC as sheath 420 is advanced into Schlemm's canal SC. This arrangement may reduce the likelihood that skiving of wall W occurs as sheath 420 is advanced into Schlemm's canal SC.

FIG. 25D is a plan view showing implant 426 disposed in Schlemm's canal SC. In the embodiment of FIG. 25D, openings 440 defined by body 428 have been uncovered. Openings 440 may be uncovered, for example, by moving sheath 420 in a proximal direction relative to implant 426. In some applications, this may be accomplished by applying a proximal directed force to sheath 420 while holding implant 426 stationary. Implant 426 may be held stationary, for example, by applying a distally directed reaction force on implant 426. In the embodiment of FIG. 25, a distally directed reaction force may be provided by pushing on a proximal end of implant 426 with a push tube.

In the embodiment of FIG. 25D, core 406 has been removed channel 438 defined by implant 426. Core 406 may be withdrawn from channel 438, for example, by moving core 406 in a proximal direction relative to implant 426. In some applications, this may be accomplished by applying a proximal directed force to core 406 while holding implant 426 stationary. Implant 426 may be held stationary, for example, by applying a distally directed reaction force on implant 426.

Figure 26D:
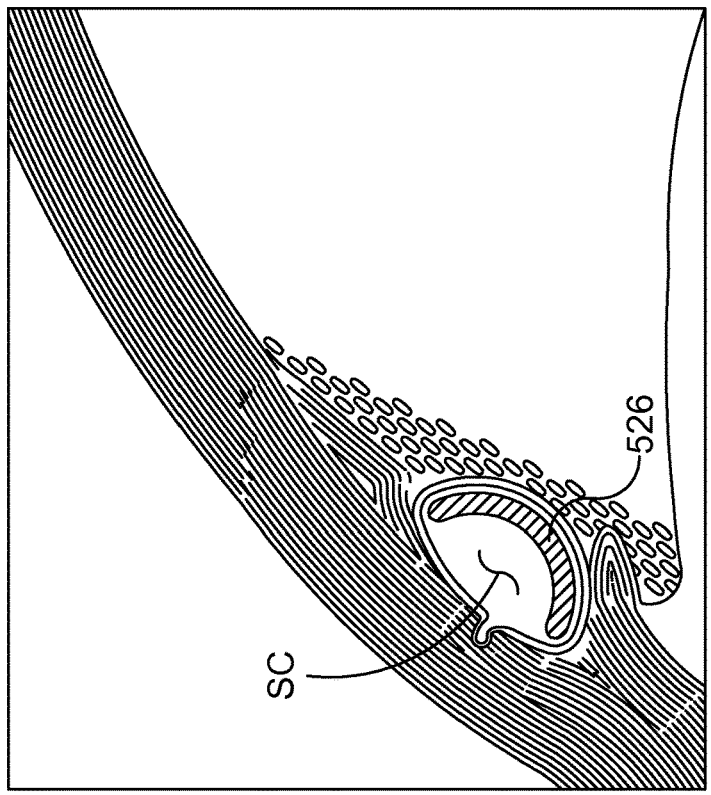

FIG. 26A through FIG. 26D are a series of section views illustrating a method in accordance with the present detailed description. The picture plane of FIG. 26A extends laterally across Schlemm's canal SC and the trabecular meshwork 596 overlaying Schlemm's canal SC. In the embodiment of FIG. 26A, the distal end of a cannula 502 has been positioned proximate Schlemm's canal SC. A method in accordance with the present detailed description may include the step of advancing the distal end of cannula 502 through the cornea of an eye so that a distal portion of cannula 502 is disposed in the anterior chamber 594 of the eye.

FIG. 26B is an additional section view showing Schlemm's canal SC shown in the previous Figure. In FIG. 26, a distal portion of cannula 502 is shown extending through a wall W of Schlemm's canal SC and trabecular meshwork 596. A distal port 504 of cannula 502 fluidly communicates with Schlemm's canal in the embodiment of FIG. 26B.

Figure 26C:
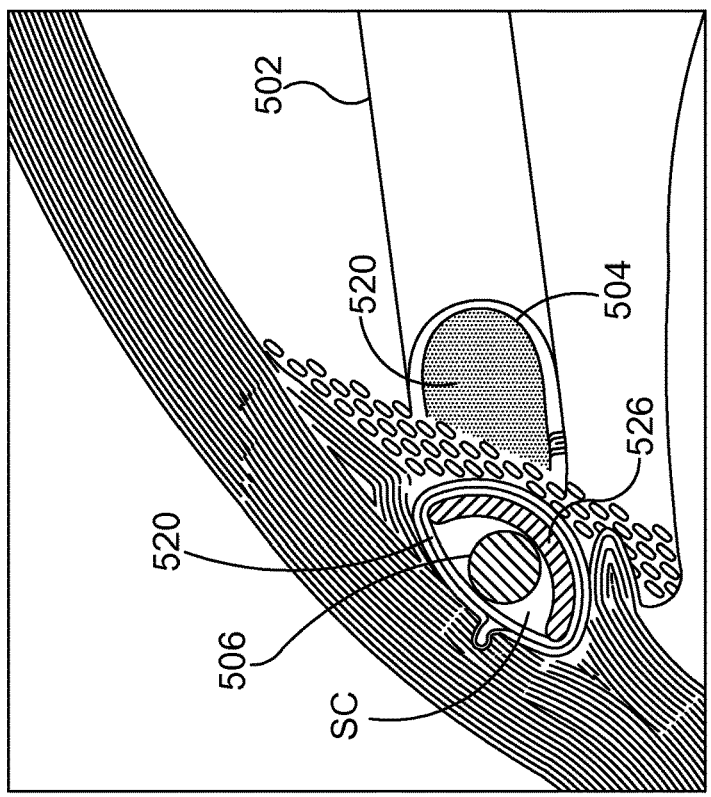

FIG. 26C is an additional section view showing Schlemm's canal SC shown in the previous Figure. In the embodiment of FIG. 26C, a distal portion of a sheath 520 is shown extending through distal port 504 of cannula 502 and into Schlemm's canal SC. Methods in accordance with the present invention can be used to deliver an implant 526 into Schlemm's canal SC. In these methods, a distal portion of sheath 520 and a core 506 may be advanced out of distal port 504 of cannula 502 and into Schlemm's canal SC. Ocular implant 526 may be disposed inside sheath 520 while the distal portion of sheath 520 is advanced into Schlemm's canal SC.

FIG. 26D is an additional section view showing implant 526 shown in the previous Figure. In the embodiment of FIG. 26, sheath 520, core 506, and cannula 502 have all been withdrawn from the eye. Implant 526 is shown resting in Schlemm's canal SC in FIG. 26.

FIG. 26 is section view illustrating an additional embodiment in accordance with the present detailed description. The picture plane of FIG. 26 extends laterally across Schlemm's canal SC and the trabecular meshwork 596 overlaying Schlemm's canal SC. In the embodiment of FIG. 26, an implant 626 is disposed in Schlemm's canal.

Figures 27A, 27B:
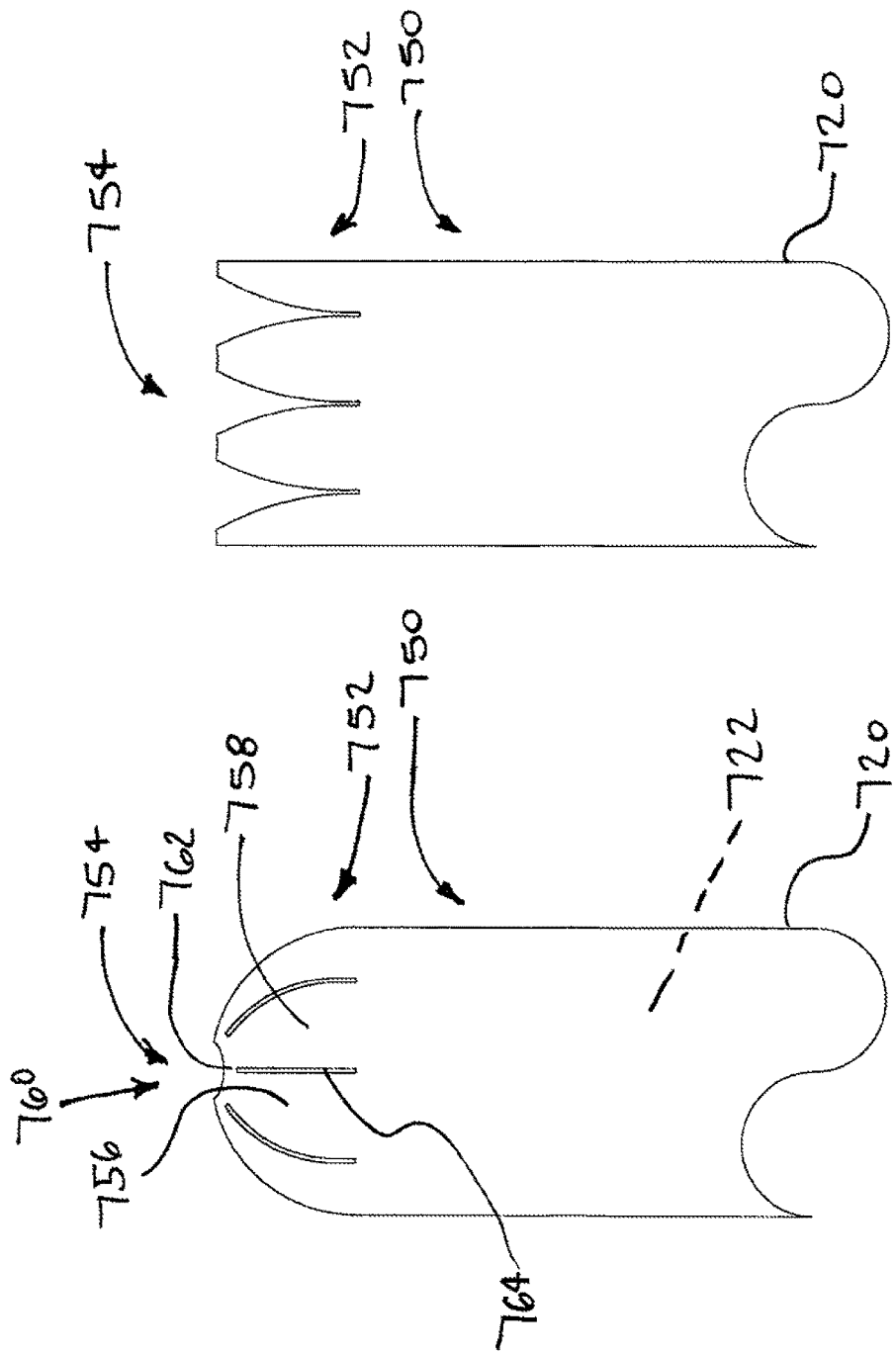
FIG. 27A and FIG. 27B are simplified plan views showing a sheath in accordance with the present detailed description.

FIG. 27A and FIG. 27B are simplified plan views showing a sheath 720 in accordance with the present detailed description. FIG. 27A and FIG. 27B may be referred to collectively as FIG. 27. Sheath 720 of FIG. 27 comprises a proximal portion 750 defining a lumen 722 and a distal portion 752 defining a distal aperture 754. With reference to FIG. 27, it will be appreciated that lumen 722 is generally larger than distal aperture 754.

In the embodiment of FIG. 27A, distal portion 752 of sheath 720 comprises a first region 756, a second region 758, and a frangible connection 760 between first region 756 and second region 758. In FIG. 27A, a first slit 764 defined by distal portion 752 is shown disposed between first region 756 and second region 758. In the embodiment of FIG. 27A, frangible connection 760 comprises a bridge 762 extending across first slit 764. With reference to FIG. 27A, it will be appreciated that distal portion 752 defines a number of slits in addition to first slit 764.

In the embodiment of FIG. 27B, frangible connection 760 has been broken. Frangible connection 760 may be selectively broken, for example, by moving sheath 720 in a proximal direction relative to an implant disposed in lumen 722 having a diameter larger than the diameters of distal opening 754 and distal portion 752 of sheath 720. With reference to FIG. 27, it will be appreciated that distal aperture 754 becomes larger when frangible connection 760 is broken.

In the embodiment of FIG. 27, the presence of slit 764 creates a localized line of weakness in distal portion 752 of sheath 720. This localized line of weakness causes distal portion 752 to selectively tear in the manner shown in FIG. 27. It is to be appreciated that distal portion 752 may comprise various elements that create a localized line of weakness without deviating from the spirit and scope of the present detailed description. Examples of possible elements include: a skive cut extending partially through the wall of distal portion 720, a series of holes extending through the wall of distal portion 720, a perf cut, a crease, and a score cut.

In FIG. 27, distal portion 752 of sheath 720 is shown extending between distal opening 754 and lumen 722. In the embodiment of FIG. 27, distal portion 752 of sheath 720 has a blunt shape. The blunt shape of distal portion 752 of sheath 720 may create a non traumatic transition that dilates Schlemm's canal as sheath 720 is advanced into Schlemm's canal. This arrangement may reduce the likelihood that skiving of the canal wall occurs as sheath 720 is advanced into Schlemm's canal.

While embodiments of the present invention have been shown and described, modifications may be made, and it is therefore intended in the appended claims to cover all such changes and modifications which fall within the true spirit and scope of the invention.

What is claimed is:

1. A method of placing an ocular implant into Schlemm's canal of a patient's eye, the ocular implant having a lateral cross section with a first lateral extent and a second lateral extent, an aspect ratio of the first lateral extent to the second lateral extent being greater than or equal to two, the method comprising:
    placing the ocular implant within Schlemm's canal with the first lateral extent oriented with a first side of Schlemm's canal and the second lateral extent oriented with a second side of Schlemm's canal, the first side of Schlemm's canal being longer than the second side;
    wherein the placing step comprises advancing the ocular implant out of a cannula into Schlemm's canal; and
    further comprising placing a distal opening of the cannula in fluid communication with Schlemm's canal.

2. The method of claim 1 further comprising advancing a distal end of the cannula through trabecular meshwork into Schlemm's canal.

3. The method of claim 1 further comprising placing a distal opening of the cannula in fluid communication with Schlemm's canal.

4. The method of claim 1 wherein the ocular implant is curved and the cannula is curved, the method further comprising orienting a curvature of the ocular implant with a curvature of the cannula.

5. The method of claim 1 wherein the ocular implant comprises a longitudinal channel and a channel opening in fluid communication with the longitudinal channel, the placing step comprising positioning the channel opening adjacent the first side of Schlemm's canal.

6. The method of claim 5 wherein the placing step comprises orienting the channel opening away from a pupil of the eye.

7. The method of claim 1 wherein the placing step comprises orienting a curvature of the ocular implant with a curvature of Schlemm's canal.

8. The method of claim 1 further comprising disposing a proximal end of the ocular implant in an anterior chamber of the eye.

9. A method of placing an ocular implant into Schlemm's canal of a patient's eye, the method comprising:
    advancing a distal end of a cannula through trabecular meshwork into Schlemm's canal;
    placing a distal opening of the cannula in fluid communication with Schlemm's canal;
    advancing the ocular implant through the distal opening of the cannula into Schlemm's canal, the ocular implant having a lateral cross section with a first lateral extent and a second lateral extent, an aspect ratio of the first lateral extent to the second lateral extent being greater than or equal to about two; and
    placing the ocular implant within Schlemm's canal with the first lateral extent oriented with a first side of Schlemm's canal and the second lateral extent oriented with a second side of Schlemm's canal, the first side of Schlemm's canal being longer than the second side.

10. The method of claim 9 wherein the ocular implant comprises a longitudinal channel and a channel opening in fluid communication with the longitudinal channel, the placing step comprising positioning the channel opening adjacent the first side of Schlemm's canal.

11. The method of claim 10 wherein the positioning step comprises orienting a curvature of the ocular implant with a curvature of Schlemm's canal.

12. The method of claim 10 wherein the positioning step comprises orienting the channel opening away from a pupil of the eye.

13. The method of claim 9 further comprising disposing a proximal end of the ocular implant in an anterior chamber of the eye.

14. The method of claim 9 wherein the ocular implant is curved and the cannula is curved, the method further comprising orienting a curvature of the ocular implant with a curvature of the cannula.

* * * * *